(12) United States Patent
Lippard et al.

(10) Patent No.: US 8,906,417 B2
(45) Date of Patent: Dec. 9, 2014

(54) NANOSTRUCTURES FOR DRUG DELIVERY

(71) Applicants: Massachusetts Institute of Technology, Cambridge, MA (US); The Brigham and Women's Hospital, Inc., Boston, MA (US)

(72) Inventors: Stephen J. Lippard, Cambridge, MA (US); Shanta Dhar, Athens, GA (US); Omid C. Farokhzad, Waban, MA (US); Frank X. Gu, Waterloo (CA); Nagesh Kolishetti, Athens, GA (US)

(73) Assignees: Massachusetts Institute of Technology, Cambridge, MA (US); The Brigham and Women's Hospital, Inc., Boston, MA (US)

( * ) Notice: Subject to any disclaimer, the term of this patent is extended or adjusted under 35 U.S.C. 154(b) by 0 days.

(21) Appl. No.: 14/075,443

(22) Filed: Nov. 8, 2013

(65) Prior Publication Data

US 2014/0079776 A1    Mar. 20, 2014

Related U.S. Application Data

(62) Division of application No. 13/122,615, filed as application No. PCT/US2009/005687 on Oct. 20, 2009, now Pat. No. 8,603,532.

(60) Provisional application No. 61/106,792, filed on Oct. 20, 2008.

(51) Int. Cl.

| | | |
|---|---|---|
| *A61K 9/14* | (2006.01) | |
| *A61K 9/48* | (2006.01) | |
| *A61K 31/555* | (2006.01) | |
| *A61K 47/48* | (2006.01) | |
| *A61K 9/51* | (2006.01) | |
| *A61K 33/24* | (2006.01) | |
| *B82Y 5/00* | (2011.01) | |

(52) U.S. Cl.
CPC . *A61K 9/48* (2013.01); *A61K 9/143* (2013.01); *A61K 31/555* (2013.01); *A61K 47/48092* (2013.01); *A61K 47/48869* (2013.01); *A61K 47/48915* (2013.01); *A61K 9/5107* (2013.01); *A61K 9/5115* (2013.01); *A61K 33/24* (2013.01); *B82Y 5/00* (2013.01)
USPC ...................................................... 424/489

(58) Field of Classification Search
None
See application file for complete search history.

(56) References Cited

U.S. PATENT DOCUMENTS

| 5,935,599 | A | 8/1999 | Dadey |
|---|---|---|---|
| 6,322,805 | B1 | 11/2001 | Kim |
| 2002/0164374 | A1 | 11/2002 | Jackson |
| 2005/0118252 | A1 | 6/2005 | Bae |
| 2005/0281883 | A1 | 12/2005 | Daniloff |
| 2007/0053845 | A1 | 3/2007 | Sengupta |
| 2007/0104654 | A1 | 5/2007 | Hsieh |
| 2007/0154398 | A1 | 7/2007 | Wang |
| 2007/0172428 | A1 | 7/2007 | Arbogast |
| 2009/0023673 | A1 | 1/2009 | Manoharan |

FOREIGN PATENT DOCUMENTS

| WO | 2005021730 | 3/2005 |
|---|---|---|
| WO | 2006052285 | 5/2006 |
| WO | 2007133807 | 11/2007 |
| WO | 2008121949 | 10/2008 |
| WO | 2009110939 | 9/2009 |
| WO | 2010008792 | 1/2010 |
| WO | 2010047765 | 4/2010 |

OTHER PUBLICATIONS

Berge, et al., "Pharmaceutical Salts", J. Pharm. Sci.,66:1-19 (1977).
Bikram, et al., "Biodegradable poly(ethylene glycol)-co-poly(L-lysine)-g-histidine multiblock copolymers for nonviral gene delivery", Macromolecule, 37:1903-16 (2004).
Bird, et al., "Single-chain antigen-binding proteins", Science, 242:423-26 (1988).
Blum, et al., "High loading efficiency and turnable release of plasmid DNA encapsulated in submicron particles fabricated from PLGA conjugated with poly-L-lysine", J controlled Release, 129(1):66-72 (2008).
Ceroritelli, et al., "PEG-SS-PPS: reduction-sensitive disulfide block copolymer vesicles for intracellular drug delivery", Biomacromolecules, 8:1966-72 (2007).
Cheng, et al., "Formulation of functionalized PLGA-PEG nanoparticles for in vivo targeted drug delivery", Biomaterials, 28:869-76 (2007).
Elbashir, et al., "Functional anatomy of siRNAs for mediating efficient RNAi in *Drosophila melanogaster* embryo lysate", EMBO J, 20:6877-88 (2001).
Farokhzad, et al., "Targeted nanoparticle-aptamer bioconjugates for cancer chemotherapy in vivo", PNAS, 103:6315-20 (2006).
General, et al., "pH-sensitive nanoparticles of poly(amino acid) dodecanoate complexes", Intl. J. Pharm., 230:11-24 (2001).
Gonzalez and Tsien, et al., "Voltage sensing by fluorescence resonance energy transfer in single cells", Biophys. J., 69:1272-80 (1995).
Gu, et al., "Precise engineering of targeted nanoparticles by using self-assembled biointegrated block copolymers", PNAS, 105:2586-91 (2007).
Hanes, et al., "Polymer microspheres for vaccine delivery", Pharm. Biotechnol., 6:389-412 (1997).

(Continued)

*Primary Examiner* — Bethany Barham
(74) *Attorney, Agent, or Firm* — Pabst Patent Group LLP

(57) ABSTRACT

The present invention provides compositions, preparations, formulations, kits, and methods useful for treating subjects having cancer or at risk of developing cancer. Some embodiments of the invention may comprise a composition comprising a plurality of particles comprising a platinum(IV) therapeutically active precursor.

22 Claims, 12 Drawing Sheets

(56) References Cited

OTHER PUBLICATIONS

Hong, et al., "Direct comparison of liposomal doxorubicin with or without polyethylene glycol coating in C-26 tumor-bearing mice: is surface coating with polyethylene glycol beneficial", Clin Cancer Res., 5:3645-52 (1999).

Huston, et al., "Protein engineering of antibody binding sites: recovery of specific activity in an anti-digoxin single-chain fv analogue produced in *Escherichia coli*", PNAS, 85:5879-83 (1988).

Kang et al., "Stimuli-sensitive nanosystems: for drug and gene delivery", Fund. Biomed. Tech., 4:161-99 (2008).

Langer, "Biomaterials in drug delivery and tissue engineering: one lavoratory's experience", Acc. Chem. Res., 33:94-101 (2000).

Owens and Peppas, "Opsonization, biodistribution, and pharmacokinetics of polymeric nanoparticles", Intl. J. Pharm., 307:93-102 (2005).

Pelisek, et al., "Optimized lipopolyplex formulations for gene transfer to human colon carcinoma cell under in vitro conditions", J Gene Med., 8:186-97 (2006).

Romberg, et al., "Sheddable coatings for long-circulating nanoparticles", Pharm. Res., 25:55-71 (2008).

Takae, et al., "PEG-detachable polyplex micelles based on disulfide-linked block catiomers as bioresponsive nonviral gene vectors", J of Am Chem. Science, 130:6001-9 (2008).

Ulrich, et al., "Polymeric systems for controlled drug release", Chemical Review, 99:3181 (1999).

Yang, et al., Evaluation of disulfide reduction during receptor-mediated endocytosis by using FRET imaging PNAS, 103:13872-77 (2006).

Zhang, et al., "Nanoparticles in medicine: therapeutic applications and developments", Clin. Pharmacol. Ther., 83:761-69 (2008).

Zhou, et al., "Investigation on a novel core-coated microspheres protein delivery system", J. Control Release, 75:27-36 (2001).

US 8,906,417 B2

NANOSTRUCTURES FOR DRUG DELIVERY

RELATED APPLICATIONS

This application is a divisional of pending application, U.S. Ser. No. 13/122,615, filed Aug. 22, 2011, entitled "Nanostructures for Drug Delivery," by Stephen J. Lippard, Shanta Dhar, Omid C. Farokhzad, Frank X. Gu, and Nagesh Kolishetti, which is a 371 application of the International Application No. PCT/US2009/05687, filed in the United States Receiving Office for the PCT on Oct. 20, 2009 divisional of U.S. Ser. No. 12/873,692, filed Sep. 1, 2010, now U.S. Pat. No. 8,323,698, issued Dec. 4, 2012, which is divisional of U.S. Ser. No. 11/803,843, filed May 15, 2007, now U.S. Pat. No. 8,367,113, issued Feb. 5, 2013, which claims the benefit of and priority to U.S. Provisional Patent Application Ser. No. 61/106,792, filed Oct. 20, 2008, entitled "Nanostructures for Drug Delivery," by Lippard, et al., herein incorporated by reference.

STATEMENT REGARDING FEDERALLY SPONSORED RESEARCH OR DEVELOPMENT

This invention was made with government support under Grant Nos. CA119349, EB003647 and CA0340992 awarded by the National Institutes of Health. The government has certain rights in the invention.

FIELD OF THE INVENTION

The present invention relates to compositions, kits, and methods for treatment of conditions suggesting a therapeutic protocol, such as cancers, using compositions that provide inhibition and/or controlled release of a drug in a patient. The compositions can include a plurality of particles and a drug or drug precursor, wherein the drug or drug precursor is compatibilized or otherwise provided in a manner such that it can be compounded with a relatively hydrophilic material, or otherwise can be compounded with hydrophilic material such as particles.

BACKGROUND OF THE INVENTION

Targeted uptake of therapeutic nanoparticles (NPs) in a cell represents a powerful technology. Such NPs have the ability to encapsulate drugs and release them through surface or bulk erosion of the particles, diffusion of the drug, and/or swelling followed by diffusion of the drug. NPs offer enormous potential for surface engineering to introduce ligands such as peptides, antibodies, and nucleic acid aptamers, which can target delivery of the drug to cells of interest. Encapsulation of a drug within the interior of the particle may also protect the drug from the external environment, thus increasing the blood circulation time of the active dose before it reaches the target. Biodegradable particles have been developed as sustained release vehicles used in the administration of small molecule drugs as well as protein and peptide drugs and nucleic acids. The drugs are typically encapsulated in a matrix (e.g. polymer matrix) which is biodegradable and biocompatible. As the matrix is degraded and/or as the drug diffuses out of the particles, the drug is released into the body. Typically, polymers may be used to prepare these particles, for example, polyesters such as poly(lactide-co-glycolide) (PLGA), polyglycolic acid, poly-beta-hydroxybutyrate, polyacrylic acid ester, etc. In some cases, a particle may also protect a drug from degradation by the body prior to release at the targeted location. Furthermore, particles can be administered using a wide variety of administration routes.

Targeting controlled release polymer systems (e.g., targeted to a particular tissue or cell type or targeted to a specific diseased tissue but not normal tissue) is desirable in many situations because it reduces the amount of a drug present in tissues of the body that are not targeted. This can be particularly important when treating a condition such as cancer where it is desirable that a cytotoxic dose of the drug is delivered to cancer cells without killing the surrounding non-cancerous tissue. Effective drug targeting may reduce the undesirable and sometimes life threatening side effects common in anticancer therapy.

In some cases, encapsulation of certain drugs or drug precursors has been met with limited success. For example, it may be difficult to encapsulate a drug or drug precursor in a particle which is suitable for delivery to a patient due to the incompatibility of the drug or drug precursor with commonly used systems for drug delivery. For example, cisplatin, an FDA approved drug for cancer treatment, is generally insoluble in organic solvents and partial solubility in water and there have been limited successes in encapsulating the cisplatin drug in certain commonly used materials for delivery (e.g., PLGA).

Accordingly, improved systems and methods are needed for delivering drugs or drug precursors in particles.

SUMMARY OF THE INVENTION

In one aspect, the invention provides a method of treating a patient in need of a therapeutic protocol. According to one set of embodiments, the method comprises administering to the patient a plurality of particles at least some of which comprise a base component and at least one small molecule drug or drug precursor comprising at least one auxiliary compatibilizing moiety selected so as to provide the drug or drug precursor with suitable compatibility with the base component so that a substantial portion of the drug or drug precursor is contained within the particles during delivery of the particles to a patient and transport of at least some of the particles to a site of delivery, wherein those particles transported to the site of delivery release a substantial portion of the drug or drug precursor at the site of delivery and participate in a chemical or biological therapeutic process.

In another aspect, the invention is directed towards a composition. According to one set of embodiments, a composition for treating a patient in need of a therapeutic protocol comprises a plurality of particles, at least some of which comprise an interior, an exterior, and a base component, with interiors more hydrophobic than exteriors, and a precursor of a substantially hydrophilic small molecule drug substantially contained within the interiors of the particles, in an amount of at least 0.1% by weight based on the weight of the particles.

In some embodiments, a method for treating a patient in need of a therapeutic protocol comprises administering to the patient a composition comprising a plurality of particles, at least some of which comprise an interior, an exterior, and a base component, with interiors more hydrophobic than exteriors, and a precursor of a substantially hydrophilic small molecule drug or drug precursor substantially contained within the interiors of the particles, wherein the maximum tolerated dose is about 1.5 times the maximum tolerated dose of the substantially hydrophilic small molecule drug or drug precursor when it is not contained within the particles.

In some cases, a method for treating a patient in need of a therapeutic protocol comprises administering to the patient a composition comprising a plurality of particles and a platinum anti-cancer drug or drug precursor substantially contained within the particles in an amount of at least about 0.1% by weight of the particles, wherein the maximum tolerated dose is about 1.5 times the maximum tolerated dose of the drug or drug precursor when it is not contained within the particles.

In some embodiments, a method for treating a patient in need of a therapeutic protocol comprises administering to the patient a composition comprising a plurality of particles, at least some of which comprise an interior, an exterior, and a base component, with interiors more hydrophobic than exteriors, and a precursor of a substantially hydrophilic small molecule drug or drug precursor substantially contained within the interiors of the particles, wherein at least about 30% of the precursor of a substantially hydrophilic small molecule drug or drug precursor is present in the blood stream of the patient at a time period of at least about 1 hour following administration of the composition.

In some cases, a method for treating a patient in need of a therapeutic protocol, comprises administering to the patient a composition comprising a plurality of particles and a platinum anti-cancer drug or drug precursor substantially contained within the particles in an amount of at least about 0.1% by weight of the particles, wherein at least about 30% of the precursor of the drug or drug precursor is present in the blood stream of the patient at a time period of at least about 1 hour following administration of the composition.

Figure 1:
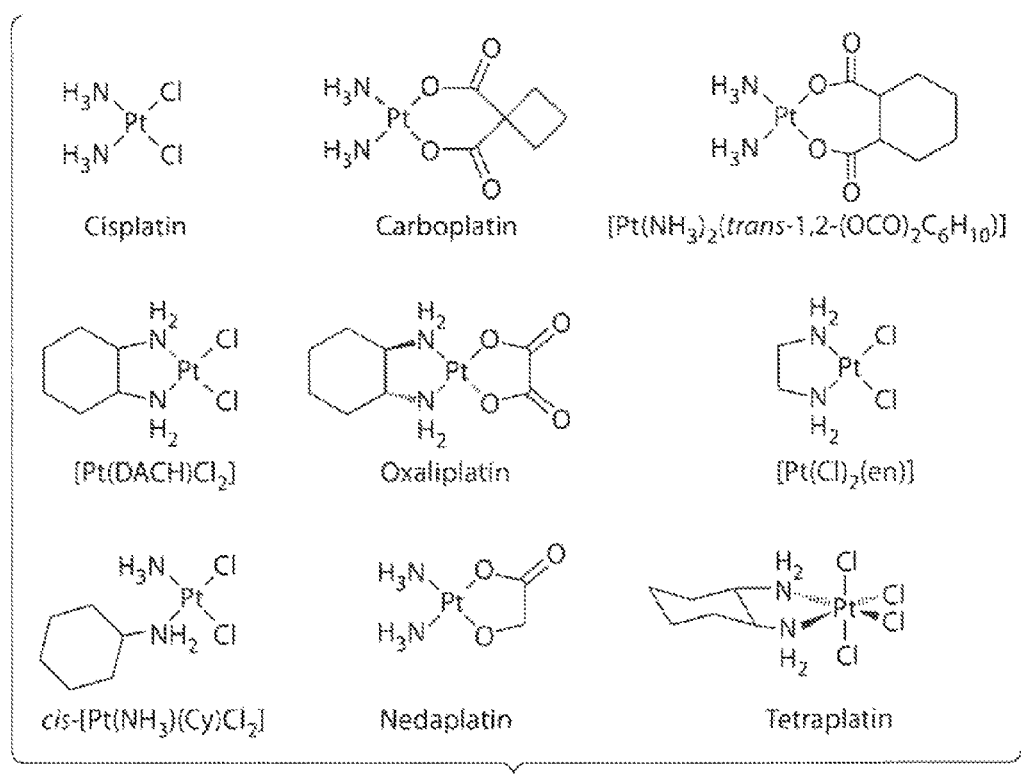
FIG. 1 shows examples of therapeutically active platinum (II) agents.

Other aspects, embodiments, and features of the invention will become apparent from the following detailed description when considered in conjunction with the accompanying drawings. The accompanying figures are schematic and are not intended to be drawn to scale. For purposes of clarity, not every component is labeled in every figure, nor is every component of each embodiment of the invention shown where illustration is not necessary to allow those of ordinary skill in the art to understand the invention. All patent applications and patents incorporated herein by reference are incorporated by reference in their entirety. In case of conflict, the present specification, including definitions, will control.

DETAILED DESCRIPTION

The invention provides compositions, preparations, formulations, kits, and methods useful for treating subjects in need of a therapeutic protocol. The subject matter of the present invention involves, in some cases, interrelated products, alternative solutions to a particular problem, and/or a plurality of different uses of one or more systems and/or articles.

The present invention relates generally to drug delivery, and more specifically to delivery of hydrophilic drugs desirably carried by relatively hydrophobic carriers (e.g., materials such as nanoparticles that can be largely polymer based). Delivery of pharmaceutical compositions of the invention can, in one set of embodiments, involve targeting to desired locations within a patient by combining material (particles) carrying the drug with a targeting moiety. Regardless of whether specific targeting is used or not, the invention provides the advantage of combining a hydrophilic drug or drug precursor with a hydrophobic component that can, if desired, at least to some extent prevent the hydrophilic drug from being dissolved by blood or other bodily fluid prematurely within a patient, e.g., prior to its delivery to a site of treatment. In one set of embodiments, drugs of the invention can comprise one or more auxiliary compatibilizing moieties that render the drug compatible with a carrier component so that the drug is not released prematurely, e.g., can be carried to the site of delivery and released. The auxiliary compatibilizing moiety can be hydrophobic, rendering an otherwise relatively hydrophilic drug compatible with relatively hydrophobic carrier which can protect it from dissolution as it passes through a patient to a site of treatment.

Throughout this disclosure, description is provided of protection or encapsulation, within a relatively hydrophobic material, of a relatively hydrophilic drug. In many instances this is described for the purpose of maintaining the drug or drug precursor encapsulated within (or compounded with) the material to control or prevent its release until the material reaches a desired site of drug delivery. In every such instance and description, it is to be understood that the invention can involve targeted delivery to a site of treatment, but need not, and while the drug might substantially remain with the delivery material prior to release at a site of delivery, it need not do so in all cases. For example, the invention can involve combination of relatively hydrophilic drug with a hydrophobic nanoparticle carrier in combination with a targeting moiety which causes the nanoparticle carrier to accumulate preferentially (although, as those of ordinary skill in the art will understand, not entirely exclusively) at a desired site of delivery at which the hydrophilic drug is released, potentially over a period of time. In other arrangements, a specific targeting moiety is not used and, in all cases, some release of the drug can occur during transport of the hydrophobic carrier material through systems of a patient (e.g., the blood stream). In its broadest sense, the invention provides at least some inhibition and/or control of release of a drug from the carrier material within a patient.

"Hydrophobic" and "hydrophilic" are given their ordinary meaning in the art and, as will be understood by those skilled in the art, in many instances herein, these are relative terms. With respect to a substantially hydrophilic drug or drug precursor, this means a molecule that has appreciable solubility in an aqueous environment. In some cases, the hydrophilic drug may be substantially soluble in water (e.g., at least about 1 g/L, at least about 5 g/L, at least about 10 g/L, etc.).

As used herein, "substantially," in connection with a drug or drug precursor being contained within a material during delivery of the material within a patient (e.g., at a site of delivery), means that at least about 25%, at least about 35%, at least about 50%, at least about 600%, at least about 75%, at least about 85%, or at least about 90% of the drug remains encapsulated in and/or compounded with the carrier material after about one minute, about five minutes, about ten minutes, about 30 minutes, about 1 hour, or about five hours of introduction of the material into a patient. In some embodiments, this may be determined by determining the amount of the drug or drug precursor remaining in the blood of a subject after a selected time period. For example, at least about 20%, about 30%, about 40%, about 50%, about 60%, about 70%, about 75%, about 80%, about 90%, or more, of the drug or drug precursor administered to a patient may be present in the blood of a subject at a time period of about 10 minutes, about 30 minutes, about 1 hour, about 2 hours, about 5 hours, or about 10 hours, following the administration of the composition. In some cases, a method of the present invention comprises administering to the subject a composition of the present invention comprising a plurality of particles and a drug or drug precursor substantially contained within the particles (e.g., a composition comprising a plurality of particles, at least some of which comprise an interior, an exterior, and a base component, with interiors more hydrophobic than exteriors, and a precursor of a substantially hydrophilic small molecule drug substantially contained within the interiors of the particles), wherein at least about 30% of the drug or drug precursor contained in the particles (e.g., the precursor of a substantially hydrophilic small molecule drug) remains in the blood stream of the subject at a time period of at least about 1 hour following administration of the composition, or any of the ranges or value described herein.

In some embodiments, a method of the present invention comprises administering to the subject a composition of the present invention comprising a plurality of particles and a drug or drug precursor substantially contained with the particles (e.g., a composition comprising a plurality of particles, at least some of which comprise an interior, an exterior, and a base component, with interiors more hydrophobic than exteriors, and a precursor of a substantially hydrophilic small molecule drug or drug precursor substantially contained within the interiors of the particles) wherein the maximum tolerated dose is about 1.5 times, about 2 times, about 2.5 times, about 3 times, about 4 times, about 5 times, about 6 times, about 7 times, about 8 times, about 9 times, about 10 times, or more, the maximum tolerated dose of the precursor of the drug or drug precursor (e.g., the substantially hydrophilic small molecule drug or drug precursor) when it is not contained within the particles. This may be due to a variety of factors, including, but not limited to (1) the slower release rate of the drug or drug precursor from the particle, thereby allowing for an extended time period over which the subject is exposed to the drug or drug precursor, and (2) localized delivery of the drug or drug precursor at a targeted site (e.g., due to particle size, the presence of targeting moieties, etc.) as opposed to systematic delivery. As will be understood by those of ordinary skill in the art, generally, delivery of a drug or drug precursor (e.g., a platinum (II) drug) may lead to an instantaneous rise in drug concentration level in the blood of a subject, whereas a drug or drug precursor contained within a particle may be provided to the subject at a slower rate, leading to comparably decreased toxicity.

The term "maximum tolerated dose," as used herein, is given its ordinary meaning in the art and refers to the maximum dose that a subject (e.g., animal species) can tolerate for a major portion of its lifetime without significant impairment or toxic effect other than carcinogenicity. Those of ordinary skill in the art will be aware of methods and techniques for determining the maximum tolerated dose of a drug or drug precursor. In some cases, the maximum tolerated dose may be determined by determining (a) overt toxicity, for example, appreciable death of cells or organ dysfunction, (b) toxic manifestations that are predicted materially to reduce the life span of the animals except as the result of neoplastic development, and/or (c) 10% or greater retardation of body weight gain as compared with control animals.

The invention presents techniques for compounding drugs or drug precursors in a variety of forms including, in one embodiment, small particles. The particles can include a relatively hydrophobic interior in which a drug or drug precursor is mixed and protected during transport to a treatment site. A wide variety of drugs can be delivered via techniques and compositions of the invention. In most embodiments, the drugs are small molecules rather than proteins or the like. Drugs can be organic, inorganic, organometallic, or the like, as describe more herein.

Drug delivery via particles is described in many locations herein. In all locations, it is to be understood that the particles can be substituted with carrier material that is not limited to any particular shape or size.

In one aspect, the invention provides methods for treating a patient in need of a therapeutic protocol. In a first set of embodiments, the method comprises administering to the patient a composition comprising a plurality of particles comprising a drug or a drug precursor, wherein the drug or drug precursor is released from the particle upon delivery to a patient. The drug or drug precursor may participate in a chemical or biological therapeutic process (e.g., treatment of a disease such as cancer). In some embodiments, at least some of the particles comprise a base component and a small molecule drug or drug precursor. The drug or drug precursor may comprise at least one auxiliary compatibilizing moiety selected so as to provide the drug or drug precursor with suitable compatibility with the base component so that the drug or drug precursor is substantially contained within the particle.

In some embodiments, compositions of the present invention may be used to delivery a drug or drug precursor to a patient, wherein the drug or drug precursor is substantially contained within a plurality of particles. The drug or drug precursor may comprise at least one auxiliary compatibilizing moiety which is selected such that the drug or drug particle is capable of being substantially contained within the particle. An "auxiliary compatibilizing moiety," as used herein, refers to a functionalization of a drug or drug precursor that provides the drug or drug precursor with suitable compatibility to the interior of a particle such that the drug or drug precursor may be substantially contained within the particle. The auxiliary compatibilizing moiety may be a species that is not needed for the drug or drug precursor to be effective in therapeutic treatment, i.e., it can be removed (and often is in accordance with use of drugs and precursors in connection with the invention) without in any way negatively affecting the therapeutic effectiveness of the drug or drug precursor. For example, the auxiliary compatibilizing moiety may provide the drug or drug precursor with the appropriate hydrophobicity or hydrophilicity to be substantially contained within a particle. The functionalization of the drug or drug precursor with the auxiliary compatibilizing moiety may allow for a drug or drug precursor to be substantially contained within a particle it would otherwise not be capable of being contained within. That is, the auxiliary compatibilizing moiety may provide the drug or drug precursor with the appropriate properties such that the drug or drug precursor can be substantially contained. As used herein, a drug or drug precursor is "substantially contained within a material" when the drug or drug precursor is essentially completely circumscribed or surrounded by the material. In some cases, the drug or drug precursor may have some portions that are substantially free of material, but at least a portion of the drug or drug precursor is essentially completely circumscribed by the material (e.g., polymer).

Non-limiting examples of properties an auxiliary compatibilizing moiety may affect of a drug or drug precursor includes hydrophobicity/hydrophilicity, acidity/basicity, ionic strength, etc. In some embodiments, a drug may be functionalized to include the auxiliary compatibilizing moiety such that the drug maintains substantially the same therapeutic effect on the patient as it did prior to functionalization. In other embodiments, a drug may be functionalized to include the auxiliary compatibilizing moiety and a drug precursor may be formed, such that the drug precursor may be activated within the patient to form the therapeutically active drug. Methods and types of auxiliary compatibilizing moieties are discussed more herein. The auxiliary compatibilizing moiety may be analyzed to determine if it provides the drug or drug precursor with the properties required for the drug or drug precursor to be substantially contained by determining the percent weight per loading of the drug or drug precursor prior to functionalization and following functionalization with the auxiliary compatibilizing moiety. For example, the weight percent of the functionalized drug or drug precursor substantially contained within the particle or other carrier material may be at least about 2 times, at least about 3 times, at least about 4 times, at least about 5 times, at least about 7 times, at least about 10 times, at least about 15 times, at least about 20 times, at least about 50 times, at least about 100 time, or greater, than the weight percent of the drug or drug precursor substantially contained within the particle prior to functionalization.

In another aspect, the invention relates to compositions for treating a patient in need of a therapeutic protocol. According to a first set of embodiments, the composition comprises a plurality of particles, wherein at least some of the particles comprise an interior, an exterior, and a base component. The interiors of the particles may be more hydrophobic than the exteriors of the particles. The particles may substantially contain a precursor of a substantially hydrophilic small drug molecule. The precursor may comprise at least one auxiliary compatibilizing moiety selected so as to provide the hydrophilic drug with substantial hydrophobicity such that it can be contained within the particle. The auxiliary compatibilizing moiety may provide the small drug molecule with enough hydrophobic character such that the drug is able to be substantially contained (e.g., at least about 0.1% by weight) wherein the drug may not be capable of being comprised within the particles if it did not comprise them moiety. It should be understood that the auxiliary compatibilizing moiety does not necessarily make the drug or drug precursor hydrophobic, but that the moiety provides the drug or drug precursor with a hydrophobic moiety such that the complex is less hydrophilic and is capable of encapsulation within the particle. Without wishing to be bound by theory, a hydrophilic drug which comprising a moiety to provide the drug with substantially hydrophobicity may aid in increasing the diffusion of the drug into a cell as compare to the drug without the moiety. This is because, in some cases, it has been found that hydrophilic drugs cannot easily diffuse across the cells through the lipid-bilayer cell membranes due to their hydrophilic nature. In some embodiments, the particles may comprise at least one targeting moiety may facilitate interaction between the particles and cells, or portions thereof, such that the precursor is released at a specific site in a patient.

In some embodiments, the drug or drug precursor may be substantially contained within the particle due to hydrophobic or hydrophilic interactions. As described herein, in some cases, the interior of a particle may be more hydrophobic than the exterior of the particle. This may aid in substantially containing the drug or drug precursor to the drug precursor in cases where the precursor is substantially hydrophobic. That is, the interaction between the interior of the particle which is more hydrophobic that the exterior may aid in substantially containing the precursor. The drug or drug precursor may comprise at least one auxiliary compatibilizing moiety selected so as to provide the precursor with suitable hydrophobicity relative to that of the interior of the particles so that the precursor is substantially contained within the particles. While much of the discussion herein focuses on providing a drug or drug precursor which is substantially hydrophobic, it should be understood, however, that this is by no mean limiting and that the alternative may occur as well, for example, in instances where in the drug or drug precursor is substantially hydrophilic. In such instances, the precursor may be substantially contained within particles, wherein the interiors of the particles are substantially more hydrophilic than the exteriors of the particles.

In some cases, the interior of the particle is more hydrophobic than the surface of the particle, which can facilitate delivery of the particle in a hydrophilic environment within a subject. For instance, the interior of the particle may be relatively hydrophobic with respect to the surface of the particle, and the drug or drug precursor may be substantially hydrophobic (e.g., via its inclusion in at least one auxiliary compatibilizing moiety), and readily associate with the relatively hydrophobic center of the particle. The drug or drug precursor may thus be contained, in large part or essentially completely within the interior of the particle, which may thus shelter it from the external environment surrounding the particle (or vice versa). For instance, a drug or drug precursor contained within a particle administered to a subject may be protected from a subject's body, and the body may also be isolated from the drug or drug precursor until the drug or drug precursor is released from the particle. In some cases, a targeting moiety present on the surface of the particle may allow the particle to become localized at a particular targeting site, for instance, a tumor, a disease site, a tissue, an organ, a type of cell, etc. The drug or drug precursor may then, in some cases, be released from the particle and allowed to interact locally, for example, with the particular targeting site.

In a particular embodiment, a method comprising administering to the patient requiring therapeutic treatment (e.g., treatment for cancer) a plurality of particles, wherein the plurality of particles comprise a Pt(IV) drug precursor and a base component. In some cases, the Pt(IV) drug precursor is substantially contained within the plurality of particles (i.e., while some of the drug or drug precursor may be present at the surface of the particles, a majority and, more typically, more than about 70%, more than about 80%, or more than about 90% of the drug or drug precursor is not present and chemically and/or biologically invisible at the surface of the particles prior to any particle degradation or drug release). Upon release from the particles, the Pt(IV) drug precursor may form a Pt(II) drug upon reduction.

The Pt(IV) substantially contained within the particles may be formed by functionalizing the Pt(II) drug with at least one auxiliary compatibilizing moieties which can allow for the delivery of the Pt(II) drug (e.g., as the Pt(IV) precursor) using particles in which the Pt(II) drug itself may not be compatible. The composition administered to the patient, may comprise a platinum(IV) therapeutically active precursor. While much of the discussion herein focuses on particles comprising a polymeric base component and a Pt(IV) drug precursor, this is by no means limiting and it should be understood that the base component may comprise other materials (e.g., liposomes, inorganic particles, metallic shells and/or particles, etc.) or other drug or drug precursor, as described more herein.

A particle may comprise an interior which is more hydrophilic that the exterior of the particle, for example, in cases where the base component of a particle comprise substantially hydrophobic portions and substantially hydrophilic portions. For example, the main chain of a polymeric base component may be substantially hydrophobic and the end groups of the polymeric base component may be substantially hydrophilic. The polymeric base component may self-assemble to form a plurality of particles such that the substantially hydrophobic components are substantially comprised within the interiors of the particles and the substantially hydrophilic components are substantially comprised within the exteriors of the particles, therefore causing the interiors of the particles to be more hydrophobic than the exteriors of the particles. As a non-limiting example, a polymeric base component may comprise poly(D,L-lactic-co-gyloclic acid) wherein the endgroup is —COOH.

Release of drug or drug precursor from particles or other carrier materials of the invention can take place via any of a host of processes known to those of ordinary skill in the art. For example, self-assembling polymeric particles of the invention (e.g., as disclosed in International Patent Application Serial No. PCT/US07/011,748, filed May 15, 2007 and published as WO2007/133807 on Nov. 22, 2007, by Gu, et al., and incorporated herein by reference) describe self-assembling polymeric compositions for admixture with and/or encapsulation of a variety of species in or on the particles. This and other known technology can be used, in combination with the specific descriptions herein, to practice the invention.

A drug or drug precursor may be substantially contained within the particle during formation of the particle, e.g., by including the agent in a solution containing the polymers that are used to form the particle, and/or the agent may be incorporated in the particle after its formation.

Many aspects of the invention involve delivery of a drug or a drug precursor with a carrier material (optionally a nanoparticle carrier material) to a site of delivery. "Site of delivery," as used herein, refers to any location within a subject where the drug is desirably released. A site of delivery can include a specific type of tissue, specific organ, node, tumor, or the like, or can simply be the circulatory system itself if that is desired. Of course, where materials are delivered to a site of delivery in accordance with the invention, not all of the material administered need necessarily go to that site and in some embodiments, much of it does not go to the desired site of delivery. Of those in ordinarily skilled in the art would understand, a particle carrying a drug, desirably delivered to the bloodstream, a tumor, or another intended site of delivery, can include a substantial fraction, typically a majority, that may not be delivered to that site but will be captured by the spleen and/or liver of a subject. Nonetheless, some of the particles will go to the site of delivery.

In some cases, the drug or drug precursor may be substantially contained within the particle until the particle becomes localized at a site of delivery (e.g., through use of a targeting moiety, as described more herein). In some instances, less than about 90%, less than about 80%, less than about 70%, less than about 60%, less than about 50%, less than about 40%, less than about 30%, less than about 20%, less than about 15%, less than about 10%, less than about 5%, less than about 1%, of the total drug or drug precursor weight percent is released from the particle prior to the particle becoming localized at a particular targeting site. In some cases, however, the drug or drug precursor may be released without delivery to a specific site, for example, within the blood stream. In such instances the drug may be released over an extended period of time, or by bursts (e.g., amounts of drug or drug precursor are released in a short period of time, followed by a periods of time where substantially no drug or drug precursor is released).

Essentially hydrophilic drugs or drug precursors of the invention can be rendered compatible with an essentially hydrophobic polymeric material, as discussed herein. An essentially hydrophobic polymeric material is one that has sufficient hydrophobicity so as to prevent significant infusion of water or aqueous fluid when the material is in solid form and exposed to an aqueous environment. Of course, materials of the invention are generally designed to be broken down in aqueous environments over time, and those of ordinary skill in the art can readily select a material, such as a polymeric material, that has sufficient hydrophobicity to provide controlled drug protection and release at a particular point and time. Although specific parameters or limitations on the meaning of a "hydrophobic material" (e.g., polymeric particle base component) would be inappropriate given different relative hydrophobicities required for different release profiles, in general, a hydrophobic base component is one that, when formed into a material suitable for a contact angle measurement, will result in a water contact angle of greater than about 50°.

The drug or drug precursor provided may be any suitable drug or drug precursor, provided the drug or drug precursor is capable of being functionalized with an auxiliary compatibilizing moiety. Functionalization, as used herein, refers to association of the drug or drug precursor with the auxiliary compatibilizing moiety in any of a number of ways including covalent bonding, coordinative coupling, or the like. Typically, the auxiliary compatibilizing moiety is covalently bound to the drug.

In some embodiments, an auxiliary compatibilizing material of the invention is one that has a hydrophobic character (optionally associated with a relative contact angle characteristic) close enough to that of the base component that it can readily mix with and be substantially compatible with a base component. With knowledge of the hydrophobicity of the base component (optionally selected for a particular release profile) and the hydrophobicity of the selected compatibilizing agent and knowledge of the hydrophilicity and/or molecular weight of the drug or drug precursor, as well as the ratio of drug or drug precursor to base component, those of ordinary skill in the art can select not only the appropriate compatibilizing moiety but also the amount of compatibilizing moiety needed as a ratio of drug or drug precursor. In some cases, one functional group or ligand of a relatively small molecular weight compatibilizing moiety can be sufficient to compound a drug or drug precursor in a hydrophobic environment. In other cases, multiple functional groups, or multiple ligands each defining a relatively large hydrophobic moiety may be required.

An auxiliary compatibilizing moiety may be associated with a drug or drug precursor, in some embodiments, via a linker, for example, CO, SiO, C(O)O, NHC(O)O, NHCO, etc. In a particular embodiment, the linker may be attached with a C(O)O linker, which may be susceptible to release of the moiety following delivery of the drug or drug precursor to the patient. In some embodiments, the auxiliary compatibilizing moiety provides a drug or drug precursor with substantially hydrophobicity. Non-limiting examples of moieties which may provide a drug or drug precursor with substantial hydrophobicity includes alkyls (e.g., hydrocarbons chains (e.g., $(CH_2)_n$), cycloalkyls (e.g., cyclohexane, adamantane, etc.), alkyl, arylalkyl, etc. In other embodiments, the auxiliary compatibilizing moiety may provide the drug or drug precursor with another desired property such as a change in the acidity/basicity (e.g., by providing acidic or basic moieties to the drug or drug precursor), ionic strength (e.g., by providing cationic/anionic moieties to the drug or drug precursor, etc.), or hydrophilicity, etc. Those of ordinary skill in the art will be aware of moieties which may provide a drug or drug precursor with suitable compatibility with the interior of a particle.

In some embodiments, the drug is a hydrophilic small drug molecule. The term "small molecule" is art-recognized and refers to a composition which has a molecular weight of less than about 2000 g/mole, less than about 1500 g/mole, less than about 1000 g/mole, less than about 800 g/mole, less than about 700 g/mole, less than about 600 g/mole, less than about 500 g/mole, less than about 400 g/mole, less than about 300 g/mole, less than about 200 g/mole, less than about 100 g/mole, or less. Those of ordinary skill in the art will be able to determine if a hydrophilic small molecule drug is suitable to be functionalized with an auxiliary compatibilizing moiety to provide the drug with the hydrophobicity required to substantially contain the drug within a particle comprising an interior more hydrophobic than the exterior. Non-limiting examples of hydrophilic drugs which may be functionalized with an auxiliary compatibilizing moiety includes dexamethasone phosphate, nicardipine hydrochloride, methylsalicylic acid, nitroglycerine, hydrophilic serotonin 5-HT$_3$ receptor antagonists (e.g., ondansetron, granisetron), aminotetralins (e.g., S(−)-2-(N-propyl-N-2-thienylethylamine)-5-hydroxytetralin), anthracyclines, etc. In some embodiments, the drug or drug precursor may comprise an inorganic or organometallic compound, for example, a platinum compound (as described herein), a ruthenium compound (e.g., trans-[RuCl$_2$(DMSO)$_4$], trans-[RuCl$_4$(imidazole)$_2$]$^-$ and trans-[RuCl$_4$(imidazole)$_2$]$^-$, etc.), cobalt compounds, copper compounds, iron compounds, etc.

In some embodiments of the present invention, the drug precursor is a platinum(IV) drug precursor. In some cases, the Pt(IV) precursor may comprise at least one ligand which functions as an auxiliary compatibilizing moiety, and is selected so that the Pt(IV) drug precursor is substantially hydrophobic, as discussed herein. That is, at least one of the auxiliary compatibilizing moieties comprise in the Pt(IV) precursor may cause the Pt(IV) precursor to be substantially hydrophobic so as to allow for association of the Pt(IV) precursor within the interior of a particle which is more hydrophobic than the exterior of the particle. The presence of the auxiliary compatibilizing moiety on the Pt(IV) center may allow for the complex to be substantially contained within a particle in which the parent Pt(II) complex (e.g., without the at least one auxiliary compatibilizing moiety) would not be capable of being substantially contained within.

The platinum(IV) drug precursor, in some embodiments, may have the formula,

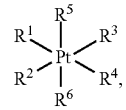

wherein $R^1$, $R^2$, $R^3$, and $R^4$ can be the same or different and each is a group comprising at least one of ammonia, an amine, a heterocycle including at least one nitrogen, an aryl group, or a leaving group, any being optionally substituted, or, any two or three of $R^1$, $R^1$, $R^3$ and $R^4$ can be joined together to form a bidentate ligand or tridentate ligand, any being optionally substituted, and $R^5$ and $R^6$ can be the same or different and comprise of the formula-$QR^7$, wherein $R^7$ is an alkyl, an alkenyl, an alkynyl, a heteroalkyl, a heteroalkenyl, a heteroalkynyl, an aryl, or a heteroaryl, and Q is O or N. In a particular embodiment, Q is O and $R^7$ is an alkyl or a heteroalkyl. Non-limiting examples of $R^7$ groups include $CO(CH_2)_nCH_3$ where n is 0, 1, 2, 3, 4, 5, 6, 7, 8, 9, or greater. As another non-limiting example, $R^7$ may comprise adamantane.

In some cases, at least one of $R^5$ or $R^6$ may be an auxiliary compatibilizing moiety and selected so as to facilitate the association of the drug precursor with an interior of a particle. In some cases, at least one of $R^5$ and $R^6$ may be selected such that the platinum(IV) drug precursor is substantially hydrophobic. For example, $R^5$ and/or $R^6$ may be substantially hydrophobic so as to aid in the association of the composition with the interior of a particle, wherein the particle comprises an interior which is more hydrophobic than the exterior of the particle. Those of ordinary skill in the art will be able to determine which ligands may aid in the formation of a substantially hydrophobic compound. For example, hydrophobic moieties that the ligand may comprise include saturated and unsaturated alkyl chains. The hydrophobic moiety may be bound to the platinum center via a heteroatom (e.g., O, N, etc.).

In some embodiments, release of $R^5$ and $R^6$ from the platinum(IV) therapeutically active precursor may form a platinum(II) therapeutically active composition. The therapeutically active platinum(II) composition may be useful for the treatment of disease, for example, cancer. In some cases, the release of $R^5$ and $R^6$ from the platinum center may be facilitated by a redox change of the platinum(IV) center. In some cases, the redox change may be caused by the release of $R^5$ and $R^6$ from the platinum(IV) center. In other cases, a redox change of the platinum(IV) center may promote the release of $R^5$ and $R^6$. For example, a redox change of the platinum(IV) center may cause a change in coordination geometry for the platinum center that reduces the number of ligands, thereby causing $R^3$ and $R^6$ to dissociate from the platinum center. As another example, the redox change of a platinum(IV) center may promote the lability of $R^5$ and $R^6$ and make it more likely that $R^5$ and $R^6$ may be replaced by other ligands.

In some embodiments, at least two of $R^1$, $R^2$, $R^3$, $R^4$, $R^5$, and $R^6$ are selected such that, upon exposure to a cellular environment, a therapeutically active platinum(II) compound forms. For example, $R^1$ and $R^2$ may be essential groups for the formation of a therapeutically active platinum agent (e.g., groups which are required for a platinum compound to be therapeutically active compound, wherein $R^3$-$R^6$ may be any variety of ligands and/or optionally absent, and at least one of $R^3$-$R^6$ is an auxiliary compatibilizing moiety). In some cases, $R^3$, $R^4$, $R^6$, and $R^6$ may be the same or different and each may be a leaving groups or a precursor to a second therapeutically active compound. In some embodiments, upon exposure to a cellular environment, $R^3$, $R^4$, $R^5$, and $R^6$ may dissociate from the platinum center, and at least two new ligands may associate with the platinum center (e.g., $R^7$ and $R^8$, as shown in Equation 1) to form a therapeutically active platinum compound (e.g., [Pt($R^1$)($R^2$)($R^7$)($R^8$)]).

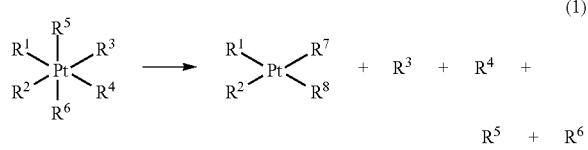

(1)

$R^7$ and $R^8$ may be the same or different and may be any suitable ligand as will be known to those of ordinary skill in the art, and are generally ligands or groups present in the environment surrounding the compound during dissociation of $R^3$, $R^4$, $R^5$ and/or $R^6$ (e.g., present in situ and/or in a cellular environment) and are capable of binding to platinum (e.g., water). It should be understood, that in some cases, less than all of $R^3$, $R^4$, $R^5$, and $R^6$ may dissociate from the platinum center and less than two ligands may associate with the platinum center. For example, $R^3$, $R^5$, and $R^6$ may dissociate from the platinum center and $R^8$ may associate, thereby forming a compound having the formula [Pt($R^1$)($R^2$)($R^3$)($R^8$)]. Those of ordinary skill in the art will be able to select appropriate combinations of ligands to form the desired therapeutically active complex.

In some cases, the at least two ligands are selected such that the ligands are cis to each other (e.g., $R^1$ and $R^2$, $R^1$ and $R^3$, $R^1$ and $R^5$, $R^1$ and $R^6$, $R^2$ and $R^4$, etc.). That is, the at least two ligands may not be trans to each other (e.g., $R^1$ and $R^4$, $R^2$ and $R^3$, $R^5$ and $R^6$). However, in some cases, the ligands may be selected such that they are trans to each other (e.g., in embodiments where the desired therapeutically active platinum agent has two essential ligands which are trans to each other). In some cases, the at least two ligands occupy equatorial positions of the compound. In some instances, however, one or more of the ligands may occupy an axial position of the compound. In some embodiments, more than two ligands may be essential for the formation of a therapeutically active platinum agent and those or ordinary skill in the art will be able to determine the required structure of the composition such that the essential ligands are present.

The platinum(IV) drug precursor may be more likely to undergo a redox change following uptake into a cell. That is, the reducing environment of a cell may reduce the platinum (IV) drug precursor to a platinum(II) drug. For example, a platinum(IV) drug precursor may not be reduced to form a platinum(II) drug prior to inclusion within a cell. That is, a redox change at the platinum center may precipitate release of the precursor to the second therapeutically active agent and will take advantage of the reducing environment found in cells.

In some embodiments, $R^1$, $R^2$, $R^3$, and $R^4$ may be selected such that, upon reduction of the platinum metal center and release of $R^5$ and $R^6$ (as described herein), a selected platinum (II) drug is formed. As another example, $R^1$, $R^2$, may be selected such that, upon reduction of the platinum metal center, release of $R^3$, $R^4$, $R^5$ and $R^6$, and association of $R^7$ and $R^8$ (as described herein), a selected platinum(II) drug is formed. For example, the $R^1$-$R^4$ may be selected such that the platinum(II) agent which forms comprises any known platinum(II) therapeutically active agent. Non-limiting examples of platinum(II) therapeutically active agents include cisplatin ([cis-Pt(NH$_3$)$_2$Cl$_2$]), carboplatin ([cis-Pt(NH$_3$)$_2$(1,1-(OCO) C$_4$H$_6$)]), oxaliplatin, [cis-Pt(NH$_3$)$_2$(trans-1,2-(OCO)$_2$ C$_6$H$_{10}$)], [cis-Pt(DACH)Cl$_2$] (where DACH is diaminocyclohexane), nedaplatin ([cis-Pt(NH$_3$)$_2$OCH$_2$CHO$_2$], stratoplatin, paraplatin, platinol, cycloplatam, dexormaplatin, enloplatin, iproplatin, lobaplatin, ormaplatin, spiroplatin, zeniplatin, etc., as will be known to those of ordinary skill in the art. FIG. 1 shows some non-limiting examples of examples of platinum(II) therapeutically active agents.

In some embodiments, $R^1$-$R^4$ will generally include functional groups capable of interaction with a metal center, e.g., heteroatoms such as nitrogen, oxygen, sulfur, and phosphorus. Non-limiting examples of compounds which $R^1$-$R^4$ may comprise include amines (primary, secondary, and tertiary), aromatic amines, amino groups, amido groups, nitro groups, nitroso groups, amino alcohols, nitriles, imino groups, isonitriles, cyanates, isocynates, phosphates, phosphonates, phosphites, (substituted) phosphines, phosphine oxides, phosphorothioates, phosphoramidates, phosphoramidites, hydroxyls, carbonyls (e.g., carboxyl, ester and formyl groups), aldehydes, ketones, ethers, carbamoyl groups, thiols, sulfides, thiocarbonyls (e.g., thiolcarboxyl, thiolester and thiolformyl groups), thioethers, mercaptans, sulfonic acids, sulfoxides, sulfates, sulfonates, sulfones, sulfonamides, sulfamoyls, and sulfinyls. In other cases, $R^1$-$R^4$ may be an aryl group, alkenyl group, alkynyl group, or other moiety which may bind the metal atom in either a sigma- or pi-coordinated fashion. In some cases, $R^1$ and $R^2$ may be labile ligands and $R^3$ and $R^4$ may be non-labile ligands covalently bonded to the platinum metal center.

In some embodiments, any two or three of $R^1$, $R^2$, $R^3$, and $R^4$ may be joined together to form a bidentate ligand or tridentate ligand. A bidentate ligand when bound to a metal center, forms a metallacycle structure with the metal center. Bidentate ligands suitable for use in the present invention include species which have at least two sites capable of binding to a metal center. For example, the bidentate ligand may comprise at least two heteroatoms that coordinate the metal center, or a heteroatom and an anionic carbon atom that coordinate the metal center. Examples of bidentate ligands suitable for use in the invention include, but are not limited to, alkyl and aryl derivatives of moieties such as amines, phosphines, phosphites, phosphates, imines, oximes, ethers, hybrids thereof, substituted derivatives there of, aryl groups (e.g., bis-aryl, heteroaryl-substituted aryl), heteroaryl groups, and the like. Specific examples of bidentate ligands include ethylene diamine, 2,2'-bipyridine, acetylacetonate, oxalate, and the like. Non-limiting examples of bidentate ligands include diimines, pyridylimines, diamines, imineamines, iminethioether, iminephosphines, bisoxazoline, bisphosphineimines, diphosphines, phosphineamine, salen and other alkoxy imine ligands, amidoamines, imidothioether fragments and alkoxyamide fragments, and combinations of the above ligands.

In some embodiments, compounds of the invention may comprise a tridentate ligand, which includes species which have at least three sites capable of binding to a metal center. For example, the tridentate ligand may comprise at least three heteroatoms that coordinate the metal center, or a combination of heteroatom(s) and anionic carbon atom(s) that coordinate the metal center. Non-limiting examples of tridentate ligands include 2,5-diiminopyridyl ligands, tripyridyl moieties, triimidazoyl moieties, tris pyrazoyl moieties, and combinations of the above ligands.

Pt(II) and Pt(IV) complexes of the invention may be synthesized according to methods known in the art, including various methods described herein. For example, the method may comprise reaction of cisplatin with one or more ligand sources. In some cases, a Pt(IV) complex, wherein $R^5$ and $R^6$ are —OH, can be obtained by reaction of the parent Pt(II) species with, for example, hydrogen peroxide at temperatures ranging between about 25° C. and about 60° C. in an appropriate solvent, such as water or N,N-dimethylformamide. The desired Pt(IV) complex comprising selected $R^5$ and $R^6$ groups may be synthesized according to method known in the art, for example, by functionalization of the —OH groups (e.g., by reaction with an anhydride, an isocyanate, a pyrocarbonate, an acid chloride, etc.).

In some embodiments, a platinum complex may comprise one or more leaving groups. As used herein, a "leaving group" is given its ordinary meaning in the art and refers to an atom or a group capable of being displaced by a nucleophile. Examples of suitable leaving groups include, but are not limited to, halides (such as chloride, bromide, and iodide), alkanesulfonyloxy, arenesulfonyloxy, alkyl-carbonyloxy (e.g., acetoxy, carboxylate), arylcarbonyloxy, mesyloxy, tosyloxy, trifluoromethane-sulfonyloxy, aryloxy, methoxy, N,O-dimethylhydroxylamino, pixyl, oxalato, malonato, and the like. A leaving group may also be a bidentate, tridentate, or other multidentate ligand. In some embodiments, the leaving group is a halide or carboxylate. In some embodiments, the leaving group is chloride.

Some embodiments of the invention comprise compounds having two leaving groups positioned in a cis configuration, i.e., the compound may be a cis isomer. However, it should be understood that compounds of the invention may also have two leaving groups positioned in a trans configuration, i.e., the compound may be a trans isomer. Those of ordinary skill in the art would understand the meaning of these terms.

Some embodiments of the invention provide the compound as a salt comprising a positively-charged platinum complex and a counterion (e.g., "X"). The counterion X may be a weak or non-nucleophilic stabilizing ion. In some cases, the counterion is a negatively-charged and/or non-coordinating ion. Examples of counterions include halides, such as chloride.

The invention also comprises homologs, analogs, derivatives, enantiomers, diastereomers, tautomers, cis- and trans-isomers, and functionally equivalent compositions of compounds described herein. "Functionally equivalent" generally refers to a composition capable of treatment of patients having a disease (e.g., cancer), or of patients susceptible to a disease. It will be understood that the skilled artisan will be able to manipulate the conditions in a manner to prepare such homologs, analogs, derivatives, enantiomers, diastereomers, tautomers, cis- and trans-isomers, and functionally equivalent compositions. Homologs, analogs, derivatives, enantiomers, diastereomers, tautomers, cis- and trans-isomers, and functionally equivalent compositions which are about as effective or more effective than the parent compound are also intended for use in the method of the invention. Such compositions may also be screened by the assays described herein for increased potency and specificity towards a disease (e.g., cancer), preferably with limited side effects. Synthesis of such compositions may be accomplished through typical chemical modification methods such as those routinely practiced in the art. Another aspect of the present invention provides any of the above-mentioned compounds as being useful for the treatment of a disease (e.g., cancer).

Another aspect of the invention is directed to systems and methods of making particles comprising a base component (e.g., a polymeric base component) and at least one drug or drug precursor (e.g., a platinum(IV) compound). In one set of embodiments, the particles are formed by providing a solution comprising at least one base component (e.g., a polymeric base component) and a therapeutically active precursor, and contacting the solution with a base component nonsolvent to produce the particle. The solution may be miscible or immiscible with the nonsolvent. In some cases, particles may be formed by pouring a first solution comprising the base component into a second solution (e.g., at a suitable rate or speed). As the first solution contacts the immiscible second liquid, particles of the base component may form. For example, precipitation of a polymeric base component upon contact with the second solution causes the polymeric base component to form nanoparticles. The precipitation of the base component may substantially encapsulate at least a portion of the therapeutically active precursor. When the rate of introduction of the first solution is carefully controlled and kept at a relatively slow rate, nanoparticles may form. The control of such particle formation can be readily optimized by one of ordinary skill in the art using routine experimentation. As a specific example, a water-miscible liquid such as acetonitrile may contain the base component, and particles may form as the acetonitrile is contacted with water, a base component nonsolvent, e.g., by pouring the acetonitrile into the water at a controlled rate. The polymeric base component contained within the solution, upon contact with the base component nonsolvent, may then precipitate to form particles such as nanoparticles.

Two liquids are said to be "immiscible" or not miscible, with each other when one is not soluble in the other to a level of at least 10% by weight at ambient temperature and pressure. Typically, an organic solution (e.g., dichloromethane, acetonitrile, chloroform, tetrahydrofuran, acetone, formamide, dimethylformamide, pyridines, dioxane, dimethysulfoxide, etc.) and an aqueous liquid (e.g., water, or water containing dissolved salts or other species, cell, or biological media, ethanol, etc.) are immiscible with respect to each other.

In some cases, the ratio of the therapeutically active precursor to the base component (e.g., polymeric base component) in a solution prior to formation of a plurality of particles may affect the percent loading of the therapeutic agent in the particle and/or the mean size of the particle. For example, an increase in the percent weight of the therapeutically active precursor to the percent weight of the base component (e.g., polymeric base component) may increase the percent loading of the therapeutically active precursor within the particle. However, the percent loading of the therapeutically active precursor in the particles formed may or may not be related to the weight percent of the therapeutically active precursor provided during formation of the particles. In some cases, the percent weight of the therapeutically active precursor provided in a solution comprising the therapeutically active precursor and the base component is at least about 5%, at least about 10%, at least about 20%, at least about 30%, at least about 40%, at least about 50%, at least about 60%, at least about 70%, at least about 80%, at least about 90%, at least about 100%, or greater, than the weight of the base component. In some cases, the percent weight is between about 5% and about 90%, between about 10% and about 80%, between about 10% and about 50%, between about 50% and about 90%, or any range therein, the weight of the base component. The percent loading of the therapeutically active precursor comprise in the plurality of particles may be greater than about 0.01%, greater than about 0.05%, greater than about 0.1%, greater than about 0.5%, greater than about 1%, greater than about 2%, greater than about 5%, greater than about 10%, greater than about 15%, greater than about 20%, greater than about 25%, greater than about 30%, greater than about 35%, greater than about 40%, greater than about 45%, greater than about 50%, greater than about 55%, or greater. In some cases, the percent loading is between about 0.01% and about 50%, between about 0.05% and about 30%, between about 0.1% and about 10%, between about 1% and about 10%, between about 0.05% and about 30%, between about 0.05% and about 10%, between about 0.1% and about 50%, or any range therein.

Without wishing to be bound by theory, the size of a particle may alter the delivery (e.g., loss of payload, drug efflux, aggregations, delivery to desired location, etc.) of a therapeutically active precursor or drug from the particles. In some cases, larger particles may lose their payload more quickly than smaller particles and/or a drug efflux may be more rapid from smaller particles than larger particles. Smaller particles, in some cases, may be more likely to aggregate than larger particles. The size of the particle may affect the distribution of the particles throughout the body. For example, larger particles injected into a bloodstream may be more likely to be lodged in small vessels than smaller particles. In some instances, larger particles may be less likely to cross biological barriers (e.g., capillary walls) than smaller particles. The size of the particles used in a delivery system may be selected based on the application, and will be readily known to those of ordinary skill in the art. For example, particles of smaller size (e.g., <200 nm) may be selected if systematic delivery of the particles throughout a patient's bloodstream is desired. As another example, particles of larger size (e.g., >200 nm) may be selected if sequestering of the particles by a patient's reticuloendothelial system upon injection is desired (e.g., sequestering of the particles in the liver, spleen, etc.). The desired length of time of delivery may also be considered when selecting particle size. For example, smaller particles may circulate in the blood stream for longer periods of time than larger particles.

In some embodiments, the particles may substantially accumulate at the site of a tumor. In some embodiments, this may be due, at least in part, the presence of a targeting moiety associated with the particle, as described herein. In some embodiments, this may be due, at least in part, due to an enhanced permeability and retention (EPR) effect, which allows for particles to accumulate specifically at a tumor site. The EPR effect will be known to those of ordinary skill in the art and refers the property by which certain sizes of material (e.g., particles) tend to accumulate in tumor tissue much more than they do in normal tissues.

In some cases, a particle may be a nanoparticle, i.e., the particle has a characteristic dimension of less than about 1 micrometer, where the characteristic dimension of a particle is the diameter of a perfect sphere having the same volume as the particle. The plurality of particles, in some embodiments, may be characterized by an average diameter (e.g., the average diameter for the plurality of particles). In some embodiments, the diameter of the particles may have a Gaussian-type distribution. In some cases, the plurality of particles may have an average diameter of less than about 300 nm, less than about 250 nm, less than about 200 nm, less than about 150 nm, less than about 100 nm, less than about 50 nm, less than about 30 nm, less than about 10 nm, less than about 3 nm, or less than about 1 nm in some cases. In some embodiments, the particles may have an average diameter of at least about 5 nm, at least about 10 nm, at least about 30 nm, at least about 50 nm, at least about 100 nm, at least about 150 nm, or greater. In some cases, the plurality of the particles have an average diameter of about nm, about 25 nm, about 50 nm, about 100 nm, about 150 nm, about 200 nm, about 250 nm, about 300 nm, about 500 nm, or the like. In some cases, the plurality of particles have an average diameter between about 10 nm and about 500 nm, between about 50 nm and about 400 nm, between about 100 nm and about 300 nm, between about 150 nm and about 250 nm, between about 175 nm and about 225 nm, or the like.

In one set of embodiments, at least a portion of the plurality of particles may each comprise at least one targeting moiety. A targeting moiety, as used herein, is a moiety able to bind to or otherwise associate with a biological moiety, for example, a membrane component, a cell surface receptor, prostate specific membrane antigen, or the like. Therefore, the targeting moiety may aid in the association and/or binding of a particle with a specific site of a patient (e.g., a certain cell type, receptor, etc.). As a non-limiting example, the targeting entity may comprise prostate specific membrane antigen which may direct the particles to prostate cells. The term "binding," as used herein, refers to the interaction between a corresponding pair of molecules or portions thereof that exhibit mutual affinity or binding capacity, typically due to specific or non-specific binding or interaction, including, but not limited to, biochemical, physiological, and/or chemical interactions. "Biological binding" defines a type of interaction that occurs between pairs of molecules including proteins, nucleic acids, glycoproteins, carbohydrates, hormones, or the like. The term "binding partner" refers to a molecule that can undergo binding with a particular molecule. "Specific binding" refers to molecules, such as polynucleotides, that are able to bind to or recognize a binding partner (or a limited number of binding partners) to a substantially higher degree than to other, similar biological entities. In one set of embodiments, the targeting moiety has a specificity (as measured via a disassociation constant) of less than about 1 micromolar, at least about 10 micromolar, or at least about 100 micromolar.

In some cases, a particle may comprise a plurality of target moieties. In some cases, the exterior and/or interior of the particle may comprise at least one targeting moiety. In some instances, the exterior of the particle can comprise a greater number of targeting moieties than the interior of the particle. In other cases, the exterior may comprise less than or about the same number of targeting moieties than the interior of the particle. In some cases, the interior of the particles may comprise essentially no targeting moieties (e.g., such that there is no detectable amount of targeting moiety present in the interior of the particles). Each of the plurality of particles comprised in a composition may or may not comprise the same number of targeting moieties as other particles within the composition.

Those of ordinary skill in the art are well aware of a wide variety of targeting moieties that can direct carrier materials such as nanoparticles to specific desired locations of a subject. An extensive body of literature exists on this subject and need not be repeated here for those of ordinary skill in the art to easily understand and widely practice aspects of the invention involving targeting. However, some examples are provided here. Non-limiting examples of biological moieties which may be employed as targeting moieties include a peptide, a protein, an enzyme, a nucleic acid, a fatty acid, a hormone, an antibody, a carbohydrate, a peptidoglycan, a glycopeptide, or the like. These and other biological moieties are discussed in detail below. In some cases, the biological moiety may be relatively large, for example, peptides, nucleic acids, or the like. For example, the biological moiety may have a molecular weight of at least about 1,000 Da, at least about 2,500 Da, at least about 3,000 Da, at least about 4,000 Da, or at least about 5,000 Da, etc. Relatively large targeting moieties may be useful, in some cases, for differentiating between cells. For instance, in some cases, smaller targeting moieties (e.g., less than about 1,000 Da) may not have adequate specificity for certain targeting applications, such as targeting applications. In contrast, larger molecular weight targeting moieties can offer a much higher targeting affinity and/or specificity. For example, a targeting moiety may offer smaller dissociation constants, e.g., tighter binding. However, in other embodiments, the targeting moiety may be relatively small, for example, having a molecular weight of less than about 1,000 Da, less than about 500 Da, or less.

In one embodiment, the targeting moiety comprises a protein or a peptide. "Proteins" and "peptides" are well-known terms in the art, and are not precisely defined in the art in terms of the number of amino acids that each includes. As used herein, these terms are given their ordinary meaning in the art. Generally, peptides are amino acid sequences of less than about 100 amino acids in length, but can include sequences of up to 300 amino acids. Proteins generally are considered to be molecules of at least 100 amino acids. A protein may be, for example, a protein drug, an antibody, an antibody fragment, a recombinant antibody, a recombinant protein, an enzyme, or the like. In some cases, one or more of the amino acids of the protein or peptide may be modified in some instances, for example, by the addition of a chemical entity such as a carbohydrate group, a phosphate group, a farnesyl group, an isofarnesyl group, a fatty acid group, a linker for conjugation, functionalization, or other modification, etc.

Other examples of peptides or proteins include, but are not limited to, ankyrins, arrestins, bacterial membrane proteins, clathrin, connexins, dystrophin, endothelin receptor, spectrin, selectin, cytokines; chemokines; growth factors, insulin, erythropoietin (EPO), tumor necrosis factor (TNF), neuropeptides, neuropeptide Y, neurotensin, transforming growth factor alpha, transforming growth factor beta, interferon (IFN), and hormones, growth inhibitors, e.g., genistein, steroids etc; glycoproteins, e.g., ABC transporters, platelet glycoproteins, GPIb-IX complex, GPIIb-IIIa complex, vitronectin, thrombomodulin, CD4, CD55, CD58, CD59, CD44, lymphocye function-associated antigen, intercellular adhesion molecule, vascular cell adhesion molecule, Thy-1, antiporters, CA-15-3 antigen, fibronectins, laminin, myelin-associated glycoprotein, GAP, GAP-43.

As used herein, an "antibody" refers to a protein or glycoprotein consisting of one or more polypeptides substantially encoded by immunoglobulin genes or fragments of immunoglobulin genes. The recognized immunoglobulin genes include the kappa, lambda, alpha, gamma, delta, epsilon, and mu constant region genes, as well as myriad immunoglobulin variable region genes. Light chains are classified as either kappa or lambda. Heavy chains are classified as gamma, mu, alpha, delta, or epsilon, which in turn define the immunoglobulin classes, IgG, IgM, IgA, IgD, and IgE, respectively. A typical immunoglobulin (antibody) structural unit is known to comprise a tetramer. Each tetramer is composed of two identical pairs of polypeptide chains, each pair having one "light" (about 25 kD) and one "heavy" chain (about 50-70 kD). The N-terminus of each chain defines a variable region of about 100 to 110 or more amino acids primarily responsible for antigen recognition. The terms variable light chain (VL) and variable heavy chain (VH) refer to these light and heavy chains respectively. Antibodies exist as intact immunoglobulins or as a number of well characterized fragments produced by digestion with various peptidases.

Non-limiting examples of antibodies and other suitable targeting moieties include anti-cluster of differentiation antigen CD-1 through CD-166 and the ligands or counter receptors for these molecules; anti-cytokine antibodies, e.g., anti-IL-1 through anti-IL-18 and the receptors for these molecules; anti-immune receptor antibodies, antibodies against T cell receptors, major histocompatibility complexes I and II, B cell receptors, selectin killer inhibitory receptors, killer activating receptors, OX-40, MadCAM-1, Gly-CAM 1, integrins, cadherens, sialoadherens, Fas, CTLA-4, Fc-gamma receptor, Fc-alpha receptors, Fc-epsilon receptors, Fc-mu receptors, and their ligands; anti-metalloproteinase antibodies, e.g., collagenase, MMP-1 through MMP-8, TIMP-1, TIMP-2; anti-cell lysis/proinflammatory molecules, e.g., perforin, complement components, prostanoids, nitrous oxide, thromboxanes; or anti-adhesion molecules, e.g., carcioembryonic antigens, lamins, or fibronectins.

Other examples of targeting moieties include cytokines or cytokine receptors, such as Interleukin-1 (IL-1), IL-2, IL-3, IL-4, IL-5, IL-6, IL-7, IL-8, IL-9, IL-10, IL 11, IL-12, IL-13, IL-14, IL-15, IL-16, IL-17, I-18, IL-1 receptor, IL-2 receptor, IL-3 receptor, IL-4 receptor, IL-5 receptor, IL-6 receptor, IL-7 receptor, IL-8 receptor, IL-9 receptor, IL-10 receptor, IL-11 receptor, IL-12 receptor, IL-13 receptor, IL-14 receptor, IL-15 receptor, IL-16 receptor, IL-17 receptor, IL-18 receptor, lymphokine inhibitory factor, macrophage colony stimulating factor, platelet derived growth factor, stem cell factor, tumor growth factor beta, tumor necrosis factor, lymphotoxin, Fas, granulocyte colony stimulating factor, granulocyte macrophage colony stimulating factor, interferon alpha, interferon beta, interferon gamma.

Still other examples of targeting moieties include growth factors and protein hormones, for example, erythropoietin, angiogenin, hepatocyte growth factor, fibroblast growth factor, keratinocyte growth factor, nerve growth factor, tumor growth factor alpha, thrombopoietin, thyroid stimulating factor, thyroid releasing hormone, neurotrophin, epidermal growth factor, VEGF, ciliary neurotrophic factor, LDL, somatomedin, insulin growth factor, or insulin-like growth factor I and II.

Additional examples of targeting moieties include chemokines, for example, ENA-78, ELC, GRO-alpha, GRO-beta, GRO-gamma, HRG, LIF, IP-10, MCP-1, MCP-2, MCP-3, MCP-4, MIP-1 alpha, MIP-1 beta, MIG, MDC, NT-3, NT-4, SCF, LIF, leptin, RANTES, lymphotactin, eotaxin-1, eotaxin-2, TARC, TECK, WAP-1, WAP-2, GCP-1, GCP-2, alpha-chemokine receptors such as CXCR1, CXCR2, CXCR3, CXCR4, CXCR5, CXCR6, CXCR7, or beta-chemokine receptors such as CCR1, CCR2, CCR3, CCR4, CCR5, CCR6, or CCR7.

In another embodiment, the targeting moiety includes a nucleic acid. The term "nucleic acids," or "oligonucleotides," as used herein, refers to a polymer of nucleotides. As used herein, a "nucleotide" is given its ordinary meaning as used in the art, i.e., a molecule comprising a sugar moiety, a phosphate group, and a base (usually nitrogenous). Typically, the nucleotide comprises one or more bases connected to a sugar-phosphate backbone (a base connected only to a sugar moiety, without the phosphate group, is a "nucleoside"). The sugars within the nucleotide may be, for example, ribose sugars (a "ribonucleic acid," or "RNA"), or deoxyribose sugars (a "deoxyribonucleic acid," or "DNA"). In some cases, the polymer may comprise both ribose and deoxyribose sugars. Examples of bases include, but not limited to, the naturally-occurring bases (e.g., adenosine or "A," thymidine or "T," guanosine or "G," cytidine or "C," or uridine or "U"). In some cases, the polymer may also comprise nucleoside analogs (e.g., aracytidine, inosine, isoguanosine, nebularine, pseudouridine, 2,6-diaminopurine, 2-aminopurine, 2-thiothymidine, 3-deaza-5-azacytidine, 2'-deoxyuridine, 3-nitorpyrrole, 4-methylindole, 4-thiouridine, 4-thiothymidine, 2-aminoadenosine, 2-thiothymidine, 2-thiouridine, 5-bromocytidine, 5-iodouridine, inosine, 6-azauridine, 6-chloropurine, 7-deazaadenosine, 7-deazaguanosine, 8-azaadenosine, 8-azidoadenosine, benzimidazole, M1-methyladenosine, pyrrolo-pyrimidine, 2-amino-6-chloropurine, 3-methyl adenosine, 5-propynylcytidine, 5-propynyluridine, 5-bromouridine, 5-fluorouridine, 5-methylcytidine, 7-deazaadenosine, 7-deazaguanosine, 8-oxoadenosine, 8-oxoguanosine, O(6)-methylguanine, 2-thiocytidine, etc.), chemically or biologically modified bases (e.g., methylated bases), intercalated bases, modified sugars (e.g., 2'-fluororibose, 2'-aminoribose, 2'-azidoribose, 2'-O-methylribose, L-enantiomeric nucleosides arabinose, hexose, etc.), modified phosphate entities (e.g., phosphorothioates or 5'-N-phosphoramidite linkages), and/or other naturally and non-naturally occurring bases substitutable into the polymer, including substituted and unsubstituted aromatic moieties. Other suitable base and/or polymer modifications are well-known to those of skill in the art. In some cases, the polynucleotide may include DNA, RNA, modified DNA, modified RNA, antisense oligonucleotides, expression plasmid systems, nucleotides, modified nucleotides, nucleosides, modified nucleosides, aptamers, intact genes, or combinations thereof. Other examples of polynucleotides include interfering RNA, natural or unnatural siRNAs, shRNAs, microRNAs, ribozymes, DNA plasmids, aptamers, antisense oligonucleotides, randomized oligonucleotides, or ribozymes.

In some embodiments, the targeting moiety may be associated with the particle prior to, during, or after formation of the particle. For example, in some cases, the base component comprised in the particles may comprise the targeting moiety prior to formation of the particle. In other cases, the targeting moiety may be associated with the base component of the particles following formation of the particle, e.g., using chemical reactions. As a non-limiting example, a particle comprising —COOH endgroups (e.g., comprised on the exterior of the particle) may be coupled with an amine functionalized targeting moiety. Those of ordinary skill in the art will be able to determine other methods and reactions for associating a targeting moiety with a particle.

As noted above, the invention involved compounding or encapsulation of a drug in or with a carrier material or base component which can be particulate. Some discussion of particulate and other materials useful in the invention are provided herein. In some embodiments, the base component may comprise a polymeric base component (e.g., a polymer). A "polymer," as used herein, is given its ordinary meaning as used in the art, i.e., a molecular structure comprising one or more repeat units (monomers), connected by covalent bonds. The repeat units may all be identical, or in some cases, there may be more than one type of repeat unit present within the polymer. In some cases, the polymer is biologically derived, i.e., a biopolymer. Non-limiting examples include peptides or proteins (i.e., polymers of various amino acids), or nucleic acids such as DNA or RNA, as discussed below. In some cases, additional moieties may also be present in the polymer, for example targeting moieties such as those described herein.

If more than one type of repeat unit is present within the polymer, then the polymer is said to be a "copolymer." It is to be understood that in any embodiment employing a polymer, the polymer being employed may be a copolymer in some cases. The repeat units forming the copolymer may be arranged in any fashion. For example, the repeat units may be arranged in a random order, in an alternating order, or as a "block" copolymer, i.e., comprising one or more regions each comprising a first repeat unit (e.g., a first block), and one or more regions each comprising a second repeat unit (e.g., a second block), etc. Block copolymers may have two (a diblock copolymer), three (a triblock copolymer), or more numbers of distinct blocks.

In some embodiments, the polymer is amphiphilic, i.e., having a hydrophilic portion and a hydrophobic portion, or a relatively hydrophilic portion and a relatively hydrophobic portion. A hydrophilic polymer is one generally that attracts water and a hydrophobic polymer is one that generally repels water. A hydrophilic or a hydrophobic polymer can be identified, for example, by preparing a sample of the polymer and measuring its contact angle with water (typically, the polymer will have a contact angle of less than about 50°, while a hydrophobic polymer will have a contact angle of greater than about 50°). In some cases, the hydrophilicity of two or more polymers may be measured relative to each other, i.e., a first polymer may be more hydrophilic than a second polymer. For instance, the first polymer may have a smaller contact angle than the second polymer.

In one set of embodiments, the polymeric base component (e.g., polymer) may be biocompatible, i.e., the polymer that does not typically induce an adverse response when inserted or injected into a living subject, for example, without significant inflammation and/or acute rejection of the polymer by the immune system, for instance, via a T-cell response. It will be recognized, of course, that "biocompatibility" is a relative term, and some degree of immune response is to be expected even for polymers that are highly compatible with living tissue. However, as used herein, "biocompatibility" refers to the acute rejection of material by at least a portion of the immune system, i.e., a non-biocompatible material implanted into a subject provokes an immune response in the subject that is severe enough such that the rejection of the material by the immune system cannot be adequately controlled, and often is of a degree such that the material must be removed from the subject. One simple test to determine biocompatibility is to expose a polymer to cells in vitro; biocompatible polymers are polymers that typically does not result in significant cell death at moderate concentrations, e.g., at concentrations of about 50 micrograms/$10^6$ cells. For instance, a biocompatible polymer may cause less than about 20% cell death when exposed to cells such as fibroblasts or epithelial cells, even if phagocytosed or otherwise uptaken by such cells. Non-limiting examples of biocompatible polymers that may be useful in various embodiments of the present invention include polydioxanone (PDO), polyhydroxyalkanoate, polyhydroxybutyrate, poly(glycerol sebacate), polyglycolide, polylactide, polycaprolactone, or copolymers or derivatives including these and/or other polymers.

In certain embodiments, the biocompatible polymer is biodegradable, i.e., the polymer is able to degrade, chemically and/or biologically, within a physiological environment, such as within the body. For instance, the polymer may be one that hydrolyzes spontaneously upon exposure to water (e.g., within a subject), the polymer may degrade upon exposure to heat (e.g., at temperatures of about 37° C.). Degradation of a polymer may occur at varying rates, depending on the polymer or copolymer used. For example, the half-life of the polymer (the time at which 50% of the polymer is degraded into monomers and/or other nonpolymeric moieties) may be on the order of days, weeks, months, or years, depending on the polymer. The polymers may be biologically degraded, e.g., by enzymatic activity or cellular machinery, in some cases, for example, through exposure to a lysozyme (e.g., having relatively low pH). In some cases, the polymers may be broken down into monomers and/or other nonpolymeric moieties that cells can either reuse or dispose of without significant toxic effect on the cells (for example, polylactide may be hydrolyzed to form lactic acid, polyglycolide may be hydrolyzed to form glycolic acid, etc.). Examples of biodegradable polymers include, but are not limited to, poly(lactide) (or poly(lactic acid)), poly(glycolide) (or poly(glycolic acid)), poly(orthoesters), poly(caprolactones), polylysine, poly(ethylene imine), poly(acrylic acid), poly(urethanes), poly(anhydrides), poly(esters), poly(trimethylene carbonate), poly(ethyleneimine), poly(acrylic acid), poly(urethane), poly(beta amino esters) or the like, and copolymers or derivatives of these and/or other polymers, for example, poly(lactide-co-glycolide) (PLGA).

In another set of embodiments, a polymer of the present invention may be able to control immunogenicity, for example a poly(alkylene glycol) (also known as poly(alkylene oxide)), such as poly(propylene glycol), or poly(ethylene oxide), also known as poly(ethylene glycol) ("PEG"), having the formula $—(CH_2—CH_2—O)_n—$, where n is any positive integer. The poly(ethylene glycol) units may be present within the polymeric base component in any suitable form. For instance, the polymeric base component may be a block copolymer where one of the blocks is poly(ethylene glycol). A polymer comprising poly(ethylene glycol) repeat units is also referred to as a "PEGylated" polymer. Such polymers can control inflammation and/or immunogenicity (i.e., the ability to provoke an immune response), due to the presence of the poly(ethylene glycol) groups.

PEGylation may also be used, in some cases, to decrease charge interaction between a polymer and a biological moiety, e.g., by creating a hydrophilic layer on the surface of the polymer, which may shield the polymer from interacting with the biological moiety. For example, PEGylation may be used to create particles which comprise an interior which is more hydrophobic than the exterior of the particles. In some cases, the addition of poly(ethylene glycol) repeat units may increase plasma half-life of the polymeric conjugate, for instance, by decreasing the uptake of the polymer by the phagocytic system while decreasing transfection/uptake efficiency by cells. Those of ordinary skill in the art will know of methods and techniques for PEGylating a polymer, for example, by using EDC (1-ethyl-3-(3-dimethylaminopropyl) carbodiimide hydrochloride) and NHS(N-hydroxysuccinimide) to react a polymer to a PEG group terminating in an amine, for example, by ring opening polymerization techniques (ROMP), or the like. In addition, certain embodiments of the invention are directed towards copolymers containing poly(ester-ether)s, e.g., polymers having repeat units joined by ester bonds (e.g., R—C(O)—O—R' bonds) and ether bonds (e.g., R—O—R' bonds).

The invention further comprises preparations, formulations, kits, and the like, comprising any of the compositions as described herein. In some cases, treatment of a disease (e.g., cancer) cancer may involve the use of compositions or "agents" as described herein. That is, one aspect of the invention involves a series of compositions (e.g., pharmaceutical compositions) or agents useful for treatment of a disease (e.g., cancer or a tumor). These compositions may also be packaged in kits, optionally including instructions for use of the composition for the treatment of such conditions. These and other embodiments of the invention may also involve promotion of the treatment of a disease (e.g., cancer or tumor) according to any of the techniques and compositions and combinations of compositions described herein.

In some embodiments, compositions and methods of the invention may be used to prevent the growth of a tumor or cancer, and/or to prevent the metastasis of a tumor or cancer. In some embodiments, compositions of the invention may be used to shrink or destroy a cancer. It should be appreciated that compositions of the invention may be used alone or in combination with one or more additional anti-cancer agents or treatments (e.g., chemotherapeutic agents, targeted therapeutic agents, pseudo-targeted therapeutic agents, hormones, radiation, surgery, etc., or any combination of two or more thereof), In some embodiments, a composition of the invention may be administered to a patient who has undergone a treatment involving surgery, radiation, and/or chemotherapy. In certain embodiments, a composition of the invention may be administered chronically to prevent, or reduce the risk of, a cancer recurrence Compositions comprising particles of the present invention, in some embodiments, may be combined with pharmaceutical acceptable carriers to form a pharmaceutical composition, according to another aspect of the invention. As would be appreciated by one of skill in this art, the carriers may be chosen based on the route of administration as described below, the location of the target issue, the drug being delivered, the time course of delivery of the drug, etc.

A "pharmaceutical compositions" or "pharmaceutically acceptable" compositions, as used herein, comprises a therapeutically effective amount of one or more of the compositions described herein, formulated together with one or more pharmaceutically acceptable carriers (additives) and/or diluents. As described in detail, the pharmaceutical compositions of the present invention may be specially formulated for administration in solid or liquid form, including those adapted for the following: oral administration, for example, drenches (aqueous or non-aqueous solutions or suspensions), tablets, e.g., those targeted for buccal, sublingual, and systemic absorption, boluses, powders, granules, pastes for application to the tongue; parenteral administration, for example, by subcutaneous, intramuscular, intravenous or epidural injection as, for example, a sterile solution or suspension, or sustained-release formulation; topical application, for example, as a cream, ointment, or a controlled-release patch or spray applied to the skin, lungs, or oral cavity; intravaginally or intrarectally, for example, as a pessary, cream or foam; sublingually; ocularly; transdermally; or nasally, pulmonary and to other mucosal surfaces.

The phrase "pharmaceutically acceptable" is employed herein to refer to those compounds, materials, compositions, and/or dosage forms which are, within the scope of sound medical judgment, suitable for use in contact with the tissues of human beings and animals without excessive toxicity, irritation, allergic response, or other problem or complication, commensurate with a reasonable benefit/risk ratio.

The phrase "pharmaceutically-acceptable carrier" as used herein means a pharmaceutically-acceptable material, composition or vehicle, such as a liquid or solid filler, diluent, excipient, or solvent encapsulating material, involved in carrying or transporting the subject compound from one organ, or portion of the body, to another organ, or portion of the body. Each carrier must be "acceptable" in the sense of being compatible with the other ingredients of the formulation and not injurious to the patient. Some examples of materials which can serve as pharmaceutically-acceptable carriers include: sugars, such as lactose, glucose and sucrose; starches, such as corn starch and potato starch; cellulose, and its derivatives, such as sodium carboxymethyl cellulose, ethyl cellulose and cellulose acetate; powdered tragacanth; malt; gelatin; talc; excipients, such as cocoa butter and suppository waxes; oils, such as peanut oil, cottonseed oil, safflower oil, sesame oil, olive oil, corn oil and soybean oil; glycols, such as propylene glycol; polyols, such as glycerin, sorbitol, mannitol and polyethylene glycol; esters, such as ethyl oleate and ethyl laurate; agar; buffering agents, such as magnesium hydroxide and aluminum hydroxide; alginic acid; pyrogen-free water; isotonic saline; Ringer's solution; ethyl alcohol; pH buffered solutions; polyesters, polycarbonates and/or polyanhydrides; and other non-toxic compatible substances employed in pharmaceutical formulations.

As set out herein, certain embodiments of the present compounds may contain a basic functional group, such as amino or alkylamino, and are, thus, capable of forming pharmaceutically-acceptable salts with pharmaceutically-acceptable acids. The term "pharmaceutically-acceptable salts" in this respect refers to the relatively non-toxic, inorganic, and organic acid addition salts of compounds of the present invention. These salts can be prepared in situ in the administration vehicle or the dosage form manufacturing process, or by separately reacting a purified compound of the invention in its free base form with a suitable organic or inorganic acid, and isolating the salt thus formed during subsequent purification. Representative salts include the hydrobromide, hydrochloride, sulfate, bisulfate, phosphate, nitrate, acetate, valerate, oleate, palmitate, stearate, laurate, benzoate, lactate, phosphate, tosylate, citrate, maleate, fumarate, succinate, tartrate, napthylate, mesylate, glucoheptonate, lactobionate, and laurylsulphonate salts and the like. (See, for example, Berge et al., "Pharmaceutical Salts," *J. Pharm. Sci.* 1977, 66, 1-19)

The pharmaceutically acceptable salts of the subject compounds include the conventional nontoxic salts or quaternary ammonium salts of the compounds, e.g., from non-toxic organic or inorganic acids. For example, such conventional nontoxic salts include those derived from inorganic acids such as hydrochloride, hydrobromic, sulfuric, sulfamic, phosphoric, nitric, and the like; and the salts prepared from organic acids such as acetic, propionic, succinic, glycolic, stearic, lactic, malic, tartaric, citric, ascorbic, palmitic, maleic, hydroxymaleic, phenylacetic, glutamic, benzoic, salicyclic, sulfanilic, 2-acetoxybenzoic, fumaric, toluenesulfonic, methanesulfonic, ethane disulfonic, oxalic, isothionic, and the like.

In other cases, the compounds of the present invention may contain one or more acidic functional groups and, thus, are capable of forming pharmaceutically-acceptable salts with pharmaceutically-acceptable bases. The term "pharmaceutically-acceptable salts" in these instances refers to the relatively non-toxic, inorganic, and organic base addition salts of compounds of the present invention. These salts can likewise be prepared in situ in the administration vehicle or the dosage form manufacturing process, or by separately reacting the purified compound in its free acid form with a suitable base, such as the hydroxide, carbonate, or bicarbonate of a pharmaceutically-acceptable metal cation, with ammonia, or with a pharmaceutically-acceptable organic primary, secondary or tertiary amine. Representative alkali or alkaline earth salts include the lithium, sodium, potassium, calcium, magnesium, and aluminum salts and the like. Representative organic amines useful for the formation of base addition salts include ethylamine, diethylamine, ethylenediamine, ethanolamine, diethanolamine, piperazine, and the like. (See, for example, Berge et al., supra).

Wetting agents, emulsifiers, and lubricants, such as sodium lauryl sulfate and magnesium stearate, as well as coloring agents, release agents, coating agents, sweetening, flavoring and perfuming agents, preservatives and antioxidants can also be present in the compositions.

Examples of pharmaceutically-acceptable antioxidants include: water soluble antioxidants, such as ascorbic acid, cysteine hydrochloride, sodium bisulfate, sodium metabisulfite, sodium sulfite and the like; oil-soluble antioxidants, such as ascorbyl palmitate, butylated hydroxyanisole (BHA), butylated hydroxytoluene (BHT), lecithin, propyl gallate, alpha-tocopherol, and the like; and metal chelating agents, such as citric acid, ethylenediamine tetraacetic acid (EDTA), sorbitol, tartaric acid, phosphoric acid, and the like.

The compositions of the present invention may be given in dosages, generally, at the maximum amount while avoiding or minimizing any potentially detrimental side effects. The compositions can be administered in effective amounts, alone or in a cocktail with other compounds, for example, other compounds that can be used to treat a disease (e.g., cancer). An effective amount is generally an amount sufficient to inhibit the disease (e.g., cancer) within the subject.

One of skill in the art can determine what an effective amount of the composition is by screening the ability of the composition using any of the assays described herein. The effective amounts may depend, of course, on factors such as the severity of the condition being treated; individual patient parameters including age, physical condition, size, and weight; concurrent treatments; the frequency of treatment; or the mode of administration. These factors are well known to those of ordinary skill in the art and can be addressed with no more than routine experimentation. In some cases, a maximum dose be used, that is, the highest safe dose according to sound medical judgment.

Actual dosage levels of the active ingredients in the pharmaceutical compositions of this invention may be varied so as to obtain an amount of the active ingredient that is effective to achieve the desired therapeutic response for a particular patient, composition, and mode of administration, without being toxic to the patient.

The selected dosage level may depend upon a variety of factors including the activity of the particular compound of the present invention employed, or the ester, salt or amide thereof, the route of administration, the time of administration, the rate of excretion or metabolism of the particular compound being employed, the duration of the treatment, other drugs, compounds and/or materials used in combination with the particular compound employed, the age, sex, weight, condition, general health and prior medical history of the patient being treated, and like factors well known in the medical arts.

A physician or veterinarian having ordinary skill in the an can readily determine and prescribe the effective amount of the pharmaceutical composition required. For example, the physician or veterinarian could start doses of the compounds of the invention employed in the pharmaceutical composition at levels lower than that required to achieve the desired therapeutic effect and then gradually increasing the dosage until the desired effect is achieved.

In some embodiments, a compound or pharmaceutical composition of the invention is provided to a subject chronically. Chronic treatments include any form of repeated administration for an extended period of time, such as repeated administrations for one or more months, between a month and a year, one or more years, or longer. In many embodiments, a chronic treatment involves administering a compound or pharmaceutical composition of the invention repeatedly over the life of the subject. For example, chronic treatments may involve regular administrations, for example one or more times a day, one or more times a week, or one or more times a month. In general, a suitable dose such as a daily dose of a compound of the invention will be that amount of the compound that is the lowest dose effective to produce a therapeutic effect. Such an effective dose will generally depend upon the factors described above. Generally doses of the compounds of this invention for a patient, when used for the indicated effects, may range from about 0.0001 to about 100 mg per kg of body weight per day. The daily dosage may range from 0.001 to 50 mg of compound per kg of body weight, or from 0.01 to about 10 mg of compound per kg of body weight. However, lower or higher doses can be used. In some embodiments, the dose administered to a subject may be modified as the physiology of the subject changes due to age, disease progression, weight, or other factors.

If desired, the effective daily dose of the active compound may be administered as two, three, four, five, six or more sub-doses administered separately at appropriate intervals throughout the day, optionally, in unit dosage forms.

While it is possible for a compound of the present invention to be administered alone, it may be administered as a pharmaceutical formulation (composition) as described above.

The compositions of the invention, in some embodiments, may be promoted for treatment of abnormal cell proliferation, diseases (e.g., cancers), or tumors, or includes instructions for treatment of accompany cell proliferation, cancers, or tumors, as mentioned above. In another aspect, the invention provides a method involving promoting the prevention or treatment of a disease (e.g., cancer) via administration of any one of the compositions of the present invention, and homologs, analogs, derivatives, enantiomers and functionally equivalent compositions thereof in which the composition is able to treat the disease. As used herein, "promoted" includes all methods of doing business including methods of education, hospital and other clinical instruction, pharmaceutical industry activity including pharmaceutical sales, and any advertising or other promotional activity including written, oral and electronic communication of any form, associated with compositions of the invention in connection with treatment of cell proliferation, diseases (e.g., cancers) or tumors. "Instructions" can define a component of promotion, and typically involve written instructions on or associated with packaging of compositions of the invention. Instructions also can include any oral or electronic instructions provided in any manner. The "kit" typically defines a package including any one or a combination of the compositions of the invention and the instructions, or homologs, analogs, derivatives, enantiomers and functionally equivalent compositions thereof, but can also include the composition of the invention and instructions of any form that are provided in connection with the composition in a manner such that a clinical professional will clearly recognize that the instructions are to be associated with the specific composition.

The kits described herein may also contain one or more containers, which can contain compounds such as the species, signaling entities, biomolecules and/or particles as described. The kits also may contain instructions for mixing, diluting, and/or administrating the compounds. The kits also can include other containers with one or more solvents, surfactants, preservatives, and/or diluents (e.g., normal saline (0.9% NaCl), or 5% dextrose) as well as containers for mixing, diluting or administering the components to the sample or to the patient in need of such treatment.

The compositions of the kit may be provided as any suitable form, for example, as liquid solutions or as dried powders. When the composition provided is a dry powder, the powder may be reconstituted by the addition of a suitable solvent, which may also be provided. In embodiments where liquid forms of the composition are sued, the liquid form may be concentrated or ready to use. The solvent may depend on the compound and the mode of use or administration. Suitable solvents for drug compositions are well known and are available in the literature.

The kit, in one set of embodiments, may comprise a carrier means being compartmentalized to receive in close confinement one or more container means such as vials, tubes, and the like, each of the container means comprising one of the separate elements to be used in the method. For example, one of the container means may comprise a positive control in the assay. Additionally, the kit may include containers for other components, for example, buffers useful in the assay.

As used herein, a "subject" or a "patient" refers to any mammal (e.g., a human), such as a mammal that may be susceptible to a disease (e.g., cancer). Examples include a human, a non-human primate, a cow, a horse, a pig, a sheep, a goat, a dog, a cat, or a rodent such as a mouse, a rat, a hamster, or a guinea pig. Generally, or course, the invention is directed toward use with humans. A subject may be a subject diagnosed with the disease or otherwise known to have the disease (e.g., cancer). In some embodiments, a subject may be diagnosed as, or known to be, at risk of developing a disease. In certain embodiments, a subject may be selected for treatment on the basis of a known disease in the subject. In some embodiments, a subject may be selected for treatment on the basis of a suspected disease in the subject. In some embodiments, a disease may be diagnosed by detecting a mutation associate in a biological sample (e.g., urine, sputum, whole blood, serum, stool, etc., or any combination thereof. Accordingly, a compound or composition of the invention may be administered to a subject based, at least in part, on the fact that a mutation is detected in at least one sample (e.g., biopsy sample or any other biological sample) obtained from the subject. In some embodiments, a cancer may not have been detected or located in the subject, but the presence of a mutation associated with a cancer in at least one biological sample may be sufficient to prescribe or administer one or more compositions of the invention to the subject. In some embodiments, the composition may be administered to prevent the development of a disease such as cancer. However, in some embodiments, the presence of an existing disease may be suspected, but not yet identified, and a composition of the invention may be administered to prevent further growth or development of the disease.

It should be appreciated that any suitable technique may be used to identify or detect mutation and/or over-expression associated with a disease such as cancer. For example, nucleic acid detection techniques (e.g., sequencing, hybridization, etc.) or peptide detection techniques (e.g., sequencing, antibody-based detection, etc.) may be used. In some embodiments, other techniques may be used to detect or infer the presence of a cancer (e.g., histology, etc.). The presence of a cancer can be detected or inferred by detecting a mutation, over-expression, amplification, or any combination thereof at one or more other loci associated with a signaling pathway of a cancer A "sample," as used herein, is any cell, body tissue, or body fluid sample obtained from a subject. Non-limiting examples of body fluids include, for example, lymph, saliva, blood, urine, and the like. Samples of tissue and/or cells for use in the various methods described herein can be obtained through standard methods including, but not limited to, tissue biopsy, including punch biopsy and cell scraping, needle biopsy; or collection of blood or other bodily fluids by aspiration or other suitable methods.

The phrase "therapeutically effective amount" as used herein means that amount of a compound, material, or composition comprising a compound of the present invention which is effective for producing some desired therapeutic effect in a subject at a reasonable benefit/risk ratio applicable to any medical treatment. Accordingly, a therapeutically effective amount prevents, minimizes, or reverses disease progression associated with a disease (e.g., cancer). Disease progression can be monitored by clinical observations, laboratory and imaging investigations apparent to a person skilled in the art. A therapeutically effective amount can be an amount that is effective in a single dose or an amount that is effective as part of a multi-dose therapy, for example an amount that is administered in two or more doses or an amount that is administered chronically.

In the compounds and compositions of the invention, the term "alkyl" refers to the radical of saturated aliphatic groups, including straight-chain alkyl groups, branched-chain alkyl groups, cycloalkyl (alicyclic) groups, alkyl substituted cycloalkyl groups, and cycloalkyl substituted alkyl groups. In some embodiments, a straight chain or branched chain alkyl may have 30 or fewer carbon atoms in its backbone, and, in some cases, 20, or fewer. In some embodiments, a straight chain or branched chain alkyl may have 12 or fewer carbon atoms in its backbone (e.g., $C_1$-$C_{12}$ for straight chain, $C_3$-$C_{12}$ for branched chain), 6 or fewer, or 4 or fewer. Likewise, cycloalkyls may have from 3-10 carbon atoms in their ring structure, or 5, 6, or 7 carbons in the ring structure. Examples of alkyl groups include, but are not limited to, methyl, ethyl, propyl, isopropyl, cyclopropyl, butyl, isobutyl, tert-butyl, cyclobutyl, hexyl, cyclochexyl, and the like.

The term "heteroalkyl" refers to an alkyl group as described herein in which one or more carbon atoms is replaced by a heteroatom. Suitable heteroatoms include oxygen, sulfur, nitrogen, phosphorus, and the like. Examples of heteroalkyl groups include, but are not limited to, alkoxy, amino, thioester, and the like.

The terms "alkenyl" and "alkynyl" refer to unsaturated aliphatic groups analogous in length and possible substitution to the alkyls described above, but that contain at least one double or triple bond respectively.

The terms "heteroalkenyl" and "heteroalkynyl" refer to unsaturated aliphatic groups analogous in length and possible substitution to the heteroalkyls described above, but that contain at least one double or triple bond respectively.

As used herein, the term "halogen" or "halide" designates —F, —Cl, —Br, or —I.

The terms "carboxyl group," "carbonyl group," and "acyl group" are recognized in the art and can include such moieties as can be represented by the general formula:

wherein W is H, OH, O-alkyl, O-alkenyl, or a salt thereof. Where W is O-alkyl, the formula represents an "ester." Where W is OH, the formula represents a "carboxylic acid." The term "carboxylate" refers to an anionic carboxyl group. In general, where the oxygen atom of the above formula is replaced by sulfur, the formula represents a "thiolcarbonyl" group. Where W is a S-alkyl, the formula represents a "thiolester." Where W is SH, the formula represents a "thiolcarboxylic acid." On the other hand, where W is alkyl, the above formula represents a "ketone" group. Where W is hydrogen, the above formula represents an "aldehyde" group.

The term "aryl" refers to aromatic carbocyclic groups, optionally substituted, having a single ring (e.g., phenyl), multiple rings (e.g., biphenyl), or multiple fused rings in which at least one is aromatic (e.g., 1,2,3,4-tetrahydronaphthyl, naphthyl, anthryl, or phenanthryl). That is, at least one ring may have a conjugated pi electron system, while other, adjoining rings can be cycloalkyls, cycloalkenyls, cycloalkynyls, aryls, and/or heterocyclyls. The aryl group may be optionally substituted, as described herein. "Carbocyclic aryl groups" refer to aryl groups wherein the ring atoms on the aromatic ring are carbon atoms. Carbocyclic aryl groups include monocyclic carbocyclic aryl groups and polycyclic or fused compounds (e.g., two or more adjacent ring atoms are common to two adjoining rings) such as naphthyl groups. In some cases, the The term "alkoxy" refers to the group, —O-alkyl.
The term "aryloxy" refers to the group, —O-aryl.
The term "acyloxy" refers to the group, —O-acyl.
The term "aralkyl" or "arylalkyl," as used herein, refers to an alkyl group substituted with an aryl group.

The terms "heteroaryl" refers to aryl groups comprising at least one heteroatom as a ring atom.

The term "heterocycle" refers to refer to cyclic groups containing at least one heteroatom as a ring atom, in some cases, 1 to 3 heteroatoms as ring atoms, with the remainder of the ring atoms being carbon atoms. Suitable heteroatoms include oxygen, sulfur, nitrogen, phosphorus, and the like. In some cases, the heterocycle may be 3- to 10-membered ring structures or 3- to 7-membered rings, whose ring structures include one to four heteroatoms. The term "heterocycle" may include heteroaryl groups, saturated heterocycles (e.g., cycloheteroalkyl) groups, or combinations thereof. The heterocycle may be a saturated molecule, or may comprise one or more double bonds. In some case, the heterocycle is a nitrogen heterocycle, wherein at least one ring comprises at least one nitrogen ring atom. The heterocycles may be fused to other rings to form a polycylic heterocycle. The heterocycle may also be fused to a spirocyclic group. In some cases, the heterocycle may be attached to a compound via a nitrogen or a carbon atom in the ring.

Heterocycles include, for example, thiophene, benzothiophene, thianthrene, furan, tetrahydrofuran, pyran, isobenzofuran, chromene, xanthene, phenoxathiin, pyrrole, dihydropyrrole, pyrrolidine, imidazole, pyrazole, pyrazine, isothiazole, isoxazole, pyridine, pyrazine, pyrimidine, pyridazine, indolizine, isoindole, indole, indazole, purine, quinolizine, isoquinoline, quinoline, phthalazine, naphthyridine, quinoxaline, quinazoline, cinnoline, pteridine, carbazole, carboline, triazole, tetrazole, oxazole, isoxazole, thiazole, isothiazole, phenanthridine, acridine, pyrimidine, phenanthroline, phenazine, phenarsazine, phenothiazine, furazan, phenoxazine, pyrrolidine, oxolane, thiolane, oxazole, oxazine, piperidine, homopiperidine (hexamethyleneimine), piperazine (e.g., N-methyl piperazine), morpholine, lactones, lactams such as azetidinones and pyrrolidinones, sultams, sultones, other saturated and/or unsaturated derivatives thereof, and the like. The heterocyclic ring can be optionally substituted at one or more positions with such substituents as described herein. In some cases, the heterocycle may be bonded to a compound via a heteroatom ring atom (e.g., nitrogen). In some cases, the heterocycle may be bonded to a compound via a carbon ring atom. In some cases, the heterocycle is pyridine, imidazole, pyrazine, pyrimidine, pyridazine, acridine, acridin-9-amine, bipyridine, naphthyridine, quinoline, benzoquinoline, benzoisoquinoline, phenanthridine-1,9-diamine, or the like.

The terms "amine" and "amino" are art-recognized and refer to both unsubstituted and substituted amines, e.g., a moiety that can be represented by the general formula: N(R') (R")(R''') wherein R', R", and R''' each independently represent a group permitted by the rules of valence. An example of a substituted amine is benzylamine.

Any of the above groups may be optionally substituted. As used herein, the term "substituted" is contemplated to include all permissible substituents of organic compounds, "permissible" being in the context of the chemical rules of valence known to those of ordinary skill in the an. It will be understood that "substituted" also includes that the substitution results in a stable compound, e.g., which does not spontaneously undergo transformation such as by rearrangement, cyclization, elimination, etc. In some cases, "substituted" may generally refer to replacement of a hydrogen with a substituent as described herein. However, "substituted," as used herein, does not encompass replacement and/or alteration of a key functional group by which a molecule is identified, e.g., such that the "substituted" functional group becomes, through substitution, a different functional group. For example, a "substituted phenyl group" must still comprise the phenyl moiety and can not be modified by substitution, in this definition, to become, e.g., a pyridine ring. In a broad aspect, the permissible substituents include acyclic and cyclic, branched and unbranched, carbocyclic and heterocyclic, aromatic and nonaromatic substituents of organic compounds. Illustrative substituents include, for example, those described herein. The permissible substituents can be one or more and the same or different for appropriate organic compounds. For purposes of this invention, the heteroatoms such as nitrogen may have hydrogen substituents and/or any permissible substituents of organic compounds described herein which satisfy the valencies of the heteroatoms.

Examples of substituents include, but are not limited to, halogen, azide, alkyl, aralkyl, alkenyl, alkynyl, cycloalkyl, hydroxyl, alkoxyl, amino, nitro, sulfhydryl, imino, amido, phosphonate, phosphinate, carbonyl, carboxyl, silyl, ether, alkylthio, sulfonyl, sulfonamido, ketone, aldehyde, ester, heterocyclyl, aromatic or heteroaromatic moieties, —$CF_3$, —CN, aryl, aryloxy, perhaloalkoxy, aralkoxy, heteroaryl, heteroaryloxy, heteroarylalkyl, heteroaralkoxy, azido, amino, halide, alkylthio, oxo, acylalkyl, carboxy esters, -carboxamido, acyloxy, aminoalkyl, alkylaminoaryl, alkylaryl, alkylaminoalkyl, alkoxyaryl, arylamino, aralkylamino, alkylsulfonyl, -carboxamidoalkylaryl, -carboxamidoaryl, hydroxyalkyl, haloalkyl, alkylaminoalkylcarboxy-, aminocarboxamidoalkyl-, cyano, alkoxyalkyl, perhaloalkyl, arylalkyloxyalkyl, and the like.

The following reference is herein incorporated by reference: U.S. Provisional Patent Application Ser. No. 61/106, 792, filed Oct. 20, 2008, entitled "Nanostructures for Drug Delivery," by Lippard, et al.

The following examples are intended to illustrate certain embodiments of the present invention, but do not exemplify the full scope of the invention.

EXAMPLE 1

Figure 2A:
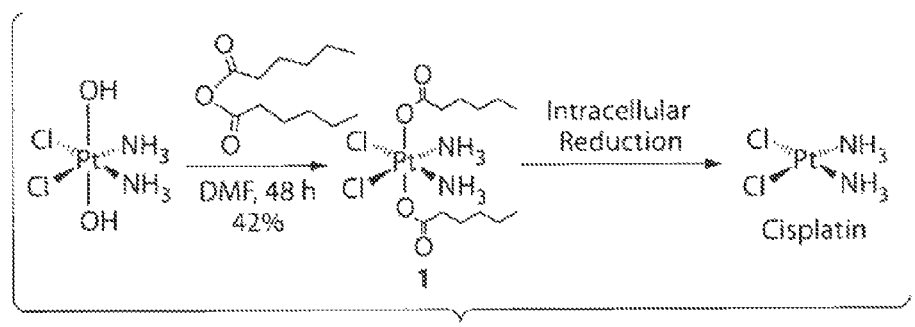
FIG. 2A is a schematic of the synthesis of a platinum(IV) precursor, compound 1, according to one embodiment of the invention.
Figure 2B:
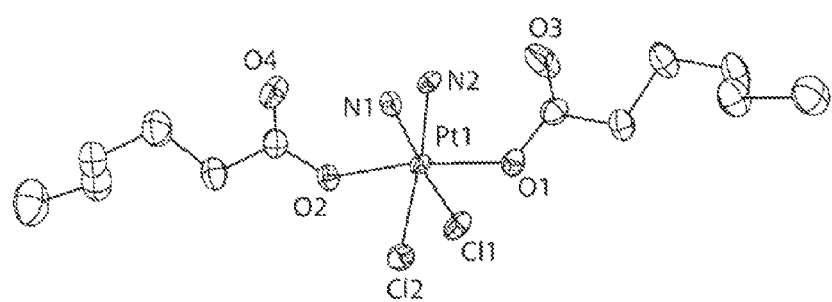
FIG. 2B shows the ORTEP diagram of compound 1 from FIG. 2A.

The following example describes the encapsulation of cisplatin into polymeric NPs. Pt(IV)-prodrug approach to deliver cisplatin using PSMA targeted pegylated PLGA NPs as the vehicle. The interior of NPs is more hydrophobic than the surface of the NPs. A hydrophobic Pt(IV) may associate with the hydrophobic center of the particles. In this example, Pt(IV)-encapsulated pegylated PLGA nanoparticle (NP) bioconjugates with a bound PSMA protein on the surface of the nanoparticles were prepared. The nanoparticles released cisplatin upon intracellular reduction. Pt(IV) compound c,c,t-[Pt(NH$_3$)$_2$(O$_2$CCH$_2$CH$_2$CH$_2$CH$_2$CH$_2$H)$_2$Cl$_2$], herein referred to as compound 1. FIG. 2A shows a scheme of the synthesis and chemical structure of compound 1 and the release of cisplatin upon intracellular reduction of compound 1. To synthesize compound 1, to a solution of c,c,t-[Pt(NH$_3$)$_2$Cl$_2$(OH)$_2$](0.69 g, 2.05 mmol) in DMSO (10 mL) was added hexanoic anhydride (0.90 g, 4.2 mmol) and the reaction mixture was stirred at room temperature for 48 hours. Water was added to the mixture and a light yellow solid precipitates, which was then dissolved in acetonitrile. Rotary evaporation of the acetonitrile solution resulted a yellow solid, which was washed several times with diethyl ether and dried. Compound 1 was isolated in 42% (0.6 g) yield. $^1$H NMR (DMSO-d$_6$) δ 6.52 (s, 6H), 2.21-2.17 (t, J=8 Hz, 4H), 1.48-1.41 (m, 4H), 1.30-1.19 (m, 8H), 0.87-0.83 (t, J=8 Hz, 6H); $^{13}$C NMR (DMSO-d$_6$) δ 180.88, 35.65, 30.87, 25.14, 22.00, 13.93; $^{195}$Pt NMR (DMSO-d$_6$); δ 1217.79 ppm. Anal. Calcd for C$_{12}$H$_{28}$Cl$_2$N$_2$O$_4$Pt: C, 27.18; H, 5.32; N, 5.28. Found: C, 27.07; H, 5.40; N, 5.19. Compound 1 was also characterized by X-ray crystallography and FIG. 2B shows the ORTEP diagram. Compound 1 crystallized in the monoclinic space group C2/c.

Nucleic acid ligands, aptamers, are a class of molecules that may overcome many drawbacks associated with antibodies in their potential for therapeutic and diagnostic applications. In some cases, aptamers have show high affinity and specificity towards the target antigens. In some cases, as opposed to other ligands, aptamers may beneficially have advantages of small size, lack of immunogenicity, and ease of isolation are well attracted for clinical trials. In this example, an A10 2'-fluoropyrimidine RNA aptamer, PSMA aptamer (Apt), was employed which recognizes the extracellular domain of PSMA. The surface of the Pt(IV)-encapsulated pegylated PLGA NPs was functionalized with this aptamer.

Copolymer PLGA-b-PEG containing terminal carboxylate groups was synthesized by amide coupling of COOH-PEG-N$_1$—H$_2$ to PLGA-COOH in methylene chloride. Pt(IV)-encapsulated NPs were prepared by using a nanoprecipitation method. PLGA-b-PEG (10 mg/mL) and compound 1 supplied at varying concentrations with respect to the polymer concentration were dissolved in acetonitrite. This mixture was slowly added to water over a period of 10 min and NPs formed in the water. The NPs were stirred at room temperature for 3 h. The NPs were washed three times using Amicon ultra centrifugation filtration membrane with a molecular weight cutoff of 100 kDa. The NP size was determined by quasi-electric laser tight scattering using a ZetaPALS dynamic tight-scattering detector (15 mW laser, incident beam=676 nm, Brookhaven Instruments). The platinum content in the NPs were measured by atomic absorption spectroscopy.

Figure 3A:
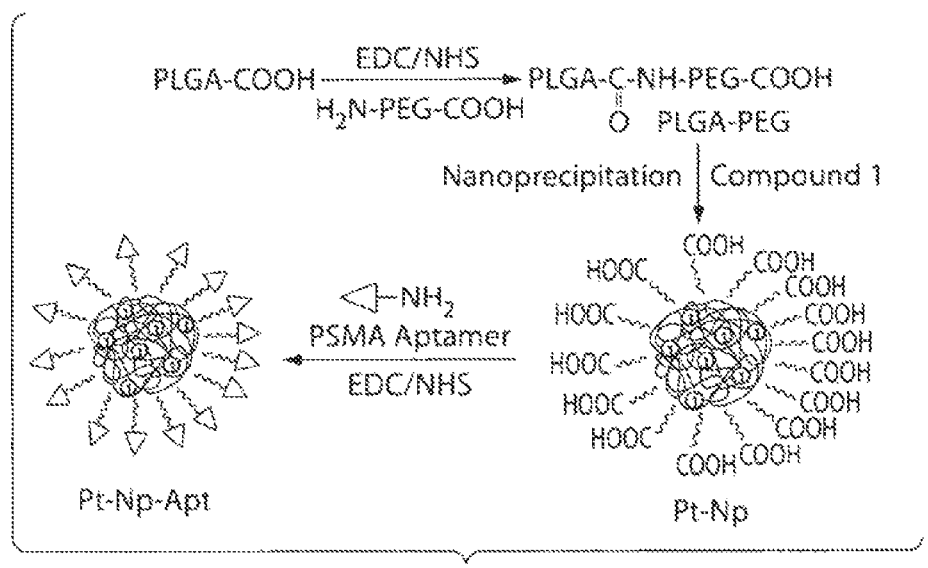
FIG. 3A shows a schematic of the formation of a particle substantially containing a platinum(IV) precursor, according to one embodiment of the present invention.
Figure 3B:
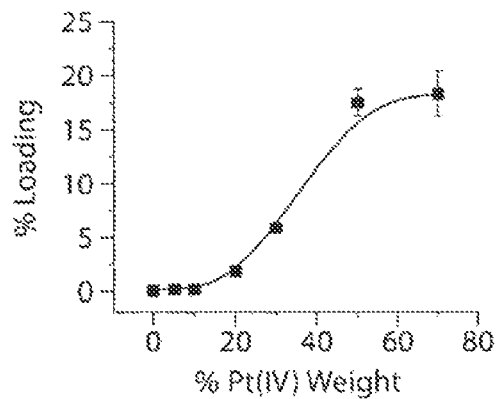
FIG. 3B shows the percent loading of a platinum(IV) precursor in a plurality of particles, according to one embodiment.
Figure 3C:
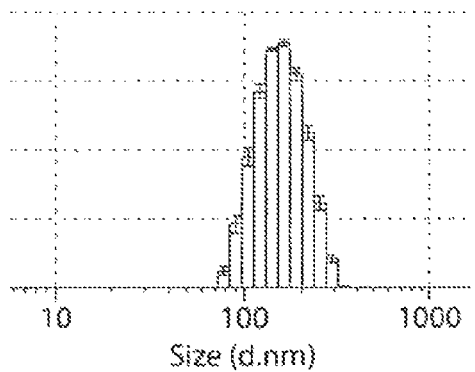
FIG. 3C shows a plot of the size of the particles substantially comprising a platinum(IV) precursor, according to one embodiment.

The Pt(IV)-encapsulated PLGA-b-PEG-COOH NP suspension in DNase RNase-free water (approximately 10 µg/µL) was allowed to react with 400 mM EDC and 100 mM NHS for 15 min at room temperature with mild agitation to give the corresponding NHS-ester. The NHS-activated NPs were washed twice using Amicon ultra centrifugation filtration membrane with a molecular weight cutoff of 100 kDa to remove unreacted NHS and conjugated to 5'-NH$_2$ modified A0 PSMA Apts of 2% weight compared to polymer concentration for 2 h at room temperature with gentle stirring. The resulting Apt conjugated Pt(IV)-encapsulated NPs, Pt-NP-Apt, were washed three times with DNase RNase-free water using Amicon filters and resuspended in PBS. FIG. 3A show a scheme of the synthesis of Pt(IV)-encapsulated PLGA-b-PEG-COOH nanoparticles by nanoprecipitation and conjugation of PSMA aptamer to the NP. For the size and loading optimizations, a series of encapsulated NPs were synthesized by varying the percent weight of compound 1 compared to polymer concentration and by using PLGA of various molecular masses. FIG. 3B shows the percent loading of compound 1 in the PLGA-b-PEG-COOH nanoparticles. FIG. 3C shows a plot of the size of the Pt(1V)-encapsulated nanoparticles. In this example, it was determined that the inherent viscosity of PLGA (0.69 dl/g in hexafluoroisoprepanol) resulted in suitably encapsulated NPs. In this example, the polydispersity of the particles showed a trend whereby it increases with the percent loading of 1 (Table 1). The size of the particles also increased with percent loading (Table 1).

TABLE 1

Pt(IV)-Encapsulated Nanoparticle Characterization.

| % Weight of 1 used | % Loading | Mean size (nm) | Polydispersity index |
|---|---|---|---|
| 5 | 0.045 | 132 ± 3.43 | 0.171 ± 0.019 |
| 10 | 0.05 | 131 ± 0.472 | 0.186 ± 0.018 |
| 20 | 1.7 | 135 ± 3.43 | 0.205 ± 0.030 |
| 30 | 5.7 | 137 ± 4.61 | 0.259 ± 0.035 |
| 50 | 17.4 | 167 ± 4.25 | 0.444 ± 0.061 |
| 70 | 18.4 | 172 ± 3.43 | 0.479 ± 0.166 |

Figure 4:
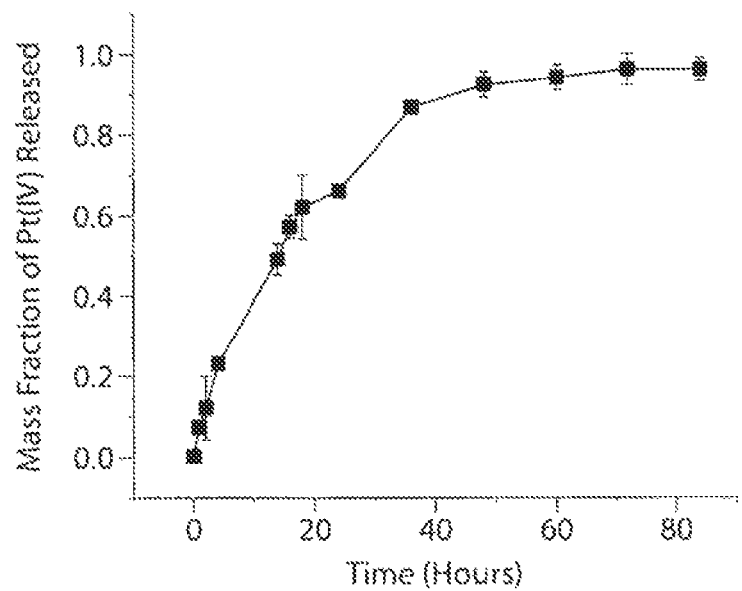
FIG. 4 shows a plot of the in vitro release kinetics of a platinum(IV) complex which was substantially contained within a plurality of particles, according to one embodiment.

For the following studies, the encapsulated particles with 5.7% loading and size of 137 rim were used. In some embodiments, as described herein, the size of the nanoparticles may play a substantial role in determining the success of their applications in drug delivery. For the release study, platinum-encapsulated NPs were dialyzed against 20 liters of PBS at approximately pH 7.4 at about 37° C. to mimic physiological conditions. The amount of platinum released from the particles was measured by platinum AAS spectroscopy. Controlled release of platinum from these NPs was achieved, as shown in FIG. 4. FIG. 4 plots the in vitro release kinetics of encapsulated Pt(IV) compound 1 from PLGA-PEG nanoparticles. The initial burst release during the first 2 hours represented only about 12% of the total platinum content. The dormant period lasted approximately 14 h (about 49%). Thereafter, a period of controlled release of platinum was observed, reaching a value of approximately 66% after about 24 h. This controlled release of platinum(IV) from the NPs extended over about 60 hours.

Figure 5A:
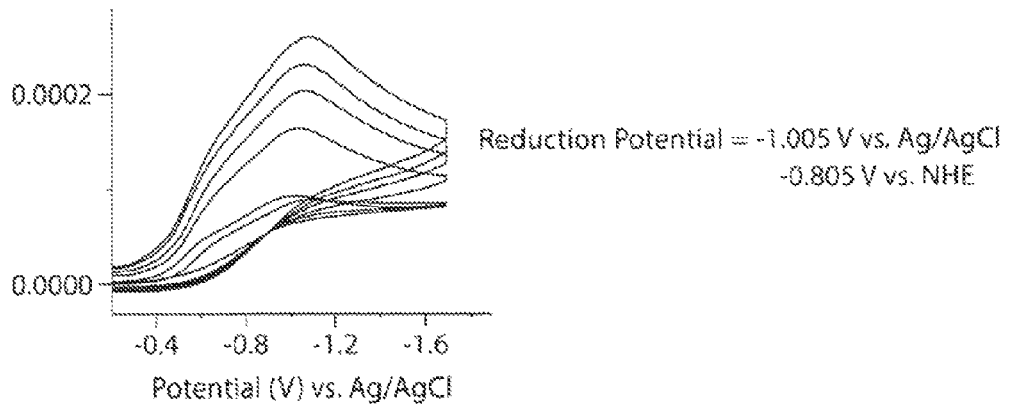
FIG. 5 shows cyclic voltammograms of compound 1 in (A) MeCN-0.1 M TBAPF$_6$, (B) 1:4 DMF-phosphate buffer-0.1M KCl of pH 7.4, and (C) 1:4 DMF-phosphate buffer-0.1M KCl of pH 6.0 with varied scan rates, according to some embodiments.
Figure 5B:
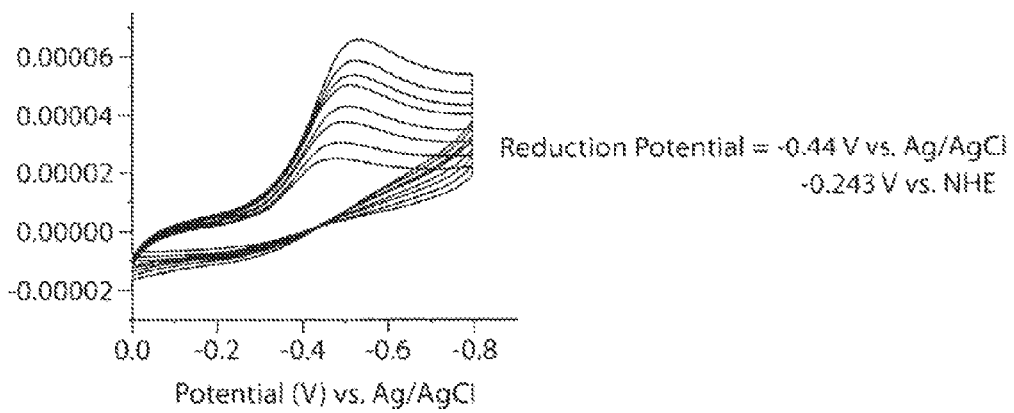
Figure 5C:
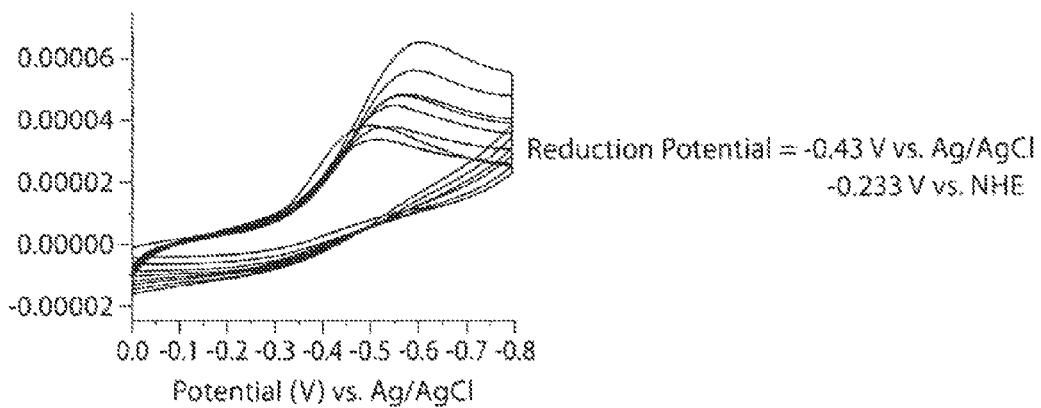

The identity of the platinum species released from the polymeric nanoparticles was determined by ESI-MS. Electron spray ionization of the PBS against which Pt-NPs were dialyzed showed a peak at 553.5, which corresponds to the sodium adduct of 1 [(M+Na')$_{calcd}$ 553.341]. Without wishing to be bound by theory, this observation may suggest that the acidic environment inside the NPs did not reduce compound 1 to its platinum(I) form, confirming that 1 remained intact after entrapment in the particles. The redox potentials were also investigated for reduction of compound 1 at various pH values. FIG. 5 shows the cyclic voltammograms of compound 1 in (A) MeCN-0.1M TBAPF$_6$, (B) 1:4 DMF-phosphate buffer-0.1M KCl of pH 7.4, and (C) 1:4 DMF-phosphate buffer-0.1M KCl of pH 6.0 with varied scan rates. These electrochemical analyses showed that complex 1 was redox-active and displayed irreversible cyclic voltammetric responses for the Pt(IV)/Pt(I) couple near −0.805 V vs. NHE in MeCN (FIG. 5A) and near −0.233 V and −0.243 V vs. NHE in a 1:4 mixture of DMF-sodium phosphate buffer of pH 7.4 (FIG. 5B) and 6.0 (FIG. 5C), respectively. The reduction potentials at various pH values suggest that in this embodiment, compound 1 may be sufficiently stable in the bloodstream after release from NPs before reaching the nuclear DNA.

Figure 6:
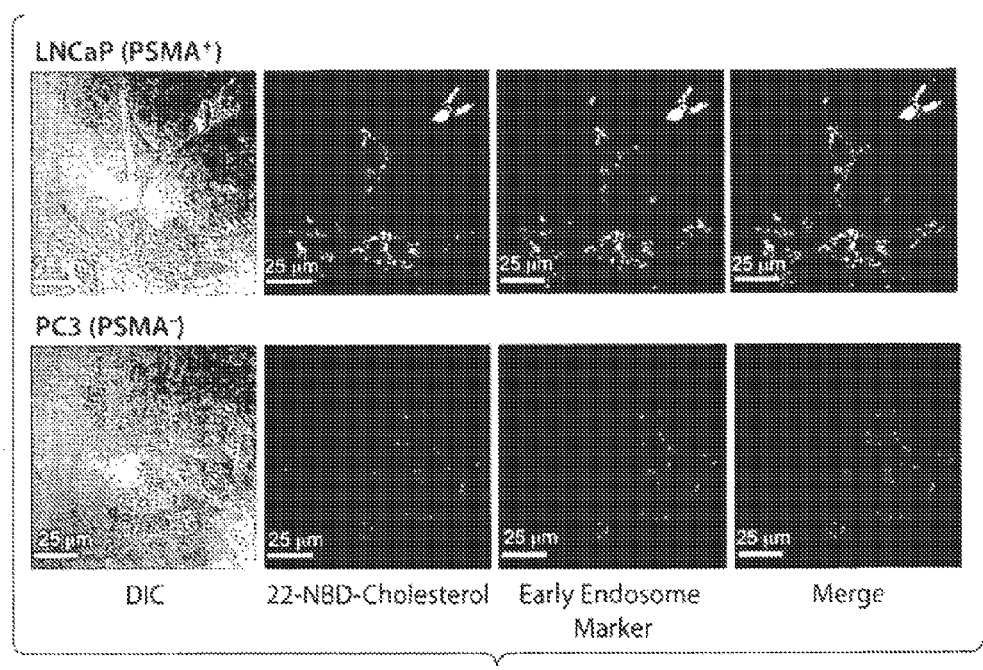
FIG. 6 shows fluorescence microscopy images of the detection of endosome formation and cellular uptake of particles comprising a platinum(IV) precursor, according to one embodiment.

Since, in some embodiments, nanoparticle uptake into cells could go through different processes, including phagocytosis and endocytosis, studies were completed to investigate the uptake mechanism. Visible evidence of targeted uptake of Pt-NP-Apt by PSMA overexpressing prostate cancer cells via endocytosis was obtained by using NPs containing compound 1 and a green fluorescent labeled cholesterol derivative, 22-NBD-cholesterol, with the use of fluorescence microscopy. PSMA is highly expressed by virtually all prostate cancers and is currently the focus of several diagnostic and therapeutic strategies for this most common cancer among men and in some instances, the LNCaP cell line serves as the best in vitro model for human prostate cancer. LNCaP produces prostate-specific biomarkers, PSMA, in a high affinity. PC-3 cells are also human prostate cancer cells that normally do not express PSMA. LNCaP (as a PSMA-over-expressing cell line, abbreviated as LNCaP(PSMA$^+$) and PC-3 (as a PC-3(PSMA) cell line) were used for the targeted localization of the compound 1 encapsulated NPs by endocytosis. FIG. 6 shows fluorescence microscopy images of the detection of endosome formation and cellular uptake of Pt-Np-Apt in LNCaP cells. Green fluorescent 22-NBD-cholesterol and compound 1 were encapsulated in the PLGA-b-PEG nanoparticles and PSMA aptamers were conjugated to the surface of the panicles. The early endosomes were visualized in red by using the early endosome marker EEA-1. As shown in FIG. 6, incubation of LNCaP cells with the Pt(IV) and cholesterol-coencapsulated NPs for 2 h and use of the early endosomal marker EEA-1 antibody showed complete internalization of these nanoparticles in the endosomes via aptamer targeted nanoparticle endocytosis. In contrast, the PSMA-PO cells do not show significant accumulation of these NPs, further supporting targeted endocytosis. From the release study mentioned above, only 12% of the total Pt(IV) was released after 2 hours in PBS at 37° C. indicating that complete internalization of these particles within 2 h is sufficient to deliver almost all the platinum(IV) content in the particles to the cells.

Figure 7A:
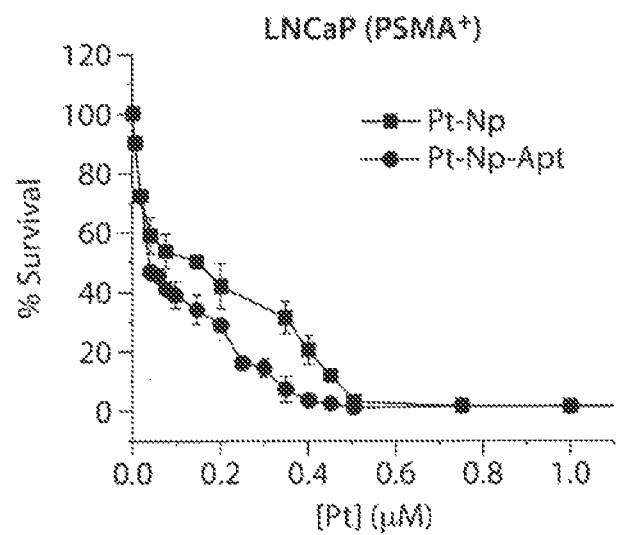
FIG. 7 shows cytotoxicity profiles of targeted (squares) and non-targeted (circles) particles comprising a platinum(IV) precursor with (A) PSMA$^+$ LNCaP cells and (B) PSMA$^+$ PC3 cells, according to some embodiments.
Figure 7B:
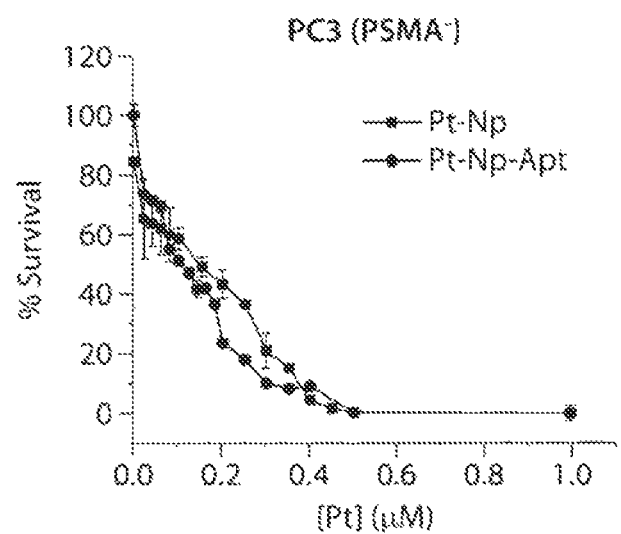

A series of in vitro cytotoxicity assays were performed to understand the anti-cancer properties of platinum(IV)-encapsulated nanoparticles, using human prostate cancer cells, and directly compared its efficacy to that of free cisplatin. The choice of the cancer cells was based on the presence of PSMA, as mentioned before. FIG. 7 shows the cytotoxicity profiles of PSMA aptamer targeted Pt(IV)-encapsulated PLGA-PEG nanoparticles (Pt-NP-Apt) (circles) and non targeted nanoparticles (Pt-NP) (squares) with (A) PSMA+ LNCaP cells and (B) PSMA+ PC3 cells after 72 h as determined by MTT assay. As shown in this figure, the Pt(IV) encapsulated polymeric nanoparticles containing PSMA aptamers on the surface (Pt-NP-Apt) were highly cytotoxic to the LNCaP cells, which up-regulate PSMA on the surface, giving an $IC_{50}$ value of 0.03 μM. Under the same conditions, the non-targeted particles (Pt-NP) give an $IC_{50}$ of 0.13 μM and the value for free cisplatin was 2.4 μM with these cells. The $IC_{50}$ of Pt-NP-Apt increased to 0.11 μM with the PSMA+ PC3 cells. The $IC_{50}$ value of the non-targeted particles (Pt-Np) with PC3 cells was comparable, the value being 0.12 μM. Free cisplatin gave an $IC_{50}$ of 0.18 μM with the PC3 cells. These results demonstrate the targeted delivery of Pt(1V) compound to the PSMA+ overexpressing LNCaP cells by the nanoparticle delivery system. The PSMA+ aptamer targeted Pt(IV)-encapsulated PLGA-b-PEG nanoparticles (Pt-Np-Apt) were 80 times more toxic in the PSMA LNCaP cells, indicating potential application of these nanoparticles in human prostate cancer.

Figure 8:
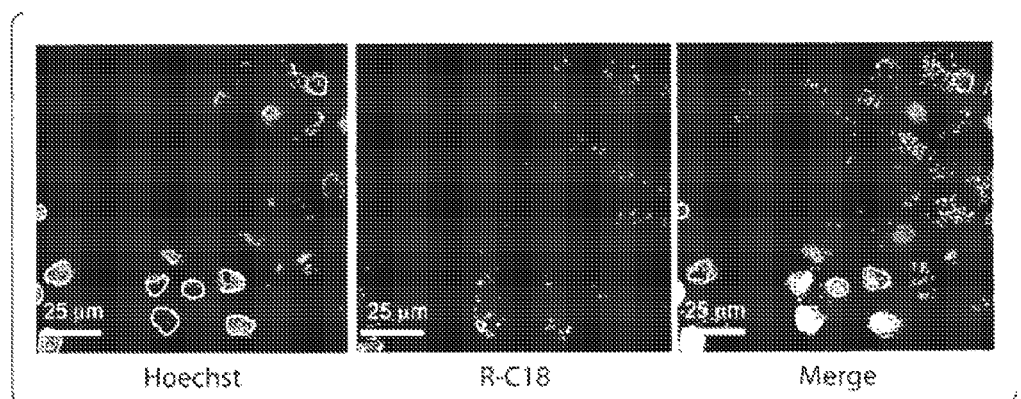
FIG. 8 shows the visualization of Pt-1,2-d(GpG) intrastrand cross-links in the nuclear DNA of LNCaP cells after treatment with a plurality of particles comprising a platinum (IV) precursor.

The anticancer activity of cisplatin is based on the formation of platination adducts with nuclear DNA. Several of these adducts have been structurally identified, of which the guanineguanine 1,2-intrastrand cross-link, cis-$(Pt(NH_3)_2d(GpG))$, represents >75% of total DNA platination. A monoclonal antibody, R—C18 specific for this adduct, was used to learn whether cisplatin released from reduction of compound 1 forms this adduct with nuclear DNA. After 12 h incubation of PSMA+ LNCaP cells with Pt-NP-Apt, formation of the 1,2-d(GpG) intrastrand cross-links was observed by antibody-derived green fluorescence in the nuclei of these cells. FIG. 8 shows the visualization of Pt-1,2-d(GpG) intrastrand cross-links in the nuclear DNA of LNCaP cells after 12 h treatment of Pt-NP-Apt. The nuclei were stained with Hoechst (left panel) and Pt-1,2-d(GpG) in DNA were visualized using Mab R—C18 (center panel). This results demonstrates the complete process by which the Pt(IV) compound 1 can be delivered to a PSMA-overexpressing prostate cancer cells via targeted nanoparticle endocytosis followed by reduction to provide a lethal dose of cisplatin, which form its signature adduct with nuclear DNA in a cell.

EXAMPLE 2

The maximum tolerated dose (MTD) of chemotherapeutic agents may be a critical factor for achieving optimal therapeutic benefit. The effectiveness of chemotherapeutic agents is generally proportional to the dose of the agents at their targets; however, the dose may be limited by systemic toxicity. In this non-limiting example, the therapeutic effectiveness of a platinum(IV) prodrug was attempted to be increased by increasing the maximum tolerated dose (MTD) of the prodrug by using a polymeric nanoparticle drug delivery systems. Various doses of cisplatin, Pt(IV)-prodrug (compound 1 from Example 1), Pt-NP (from Example 1), or PLGA-PEG-NP (control, nanoparticles not comprising platinum complexes) were injected intravenously and the MTD was estimated based on the threshold at which all mice survived.

Figure 9:
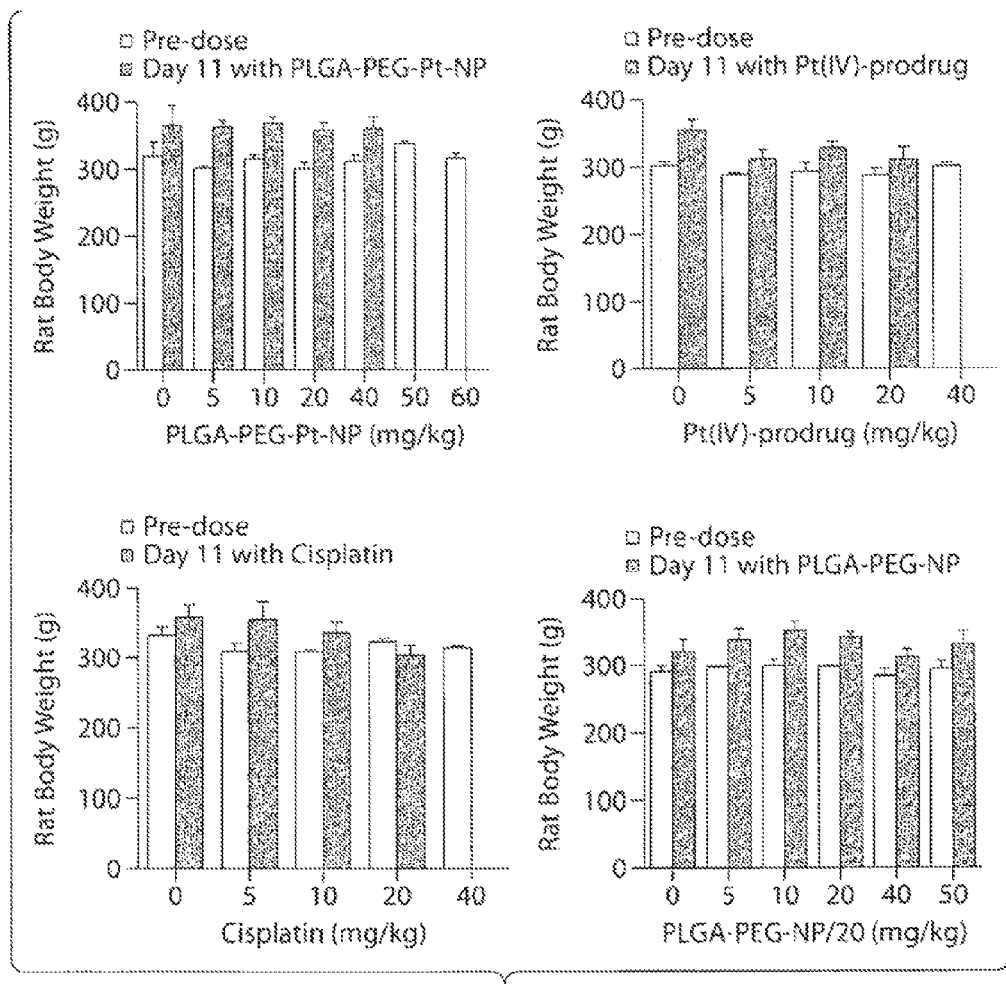
FIG. 9 shows the body weight change after treatment of rats with Pt-NPs, cisplatin, and PLGA-PEG-NPs, according to non-limiting embodiments.

Male Sprague Dawley Rats were used for MTD determination with intravenous administration. Dosing and survival details are summarized in Table 2. All rats treated with plain nanoparticles tolerated these doses. In the Pt-NP group, rats receiving doses up to 40 mg/kg tolerated the dose, but two of three in the 50 and 60-mg/kg groups died. Only the dose of 20 mg/kg free cisplatin or Pt(IV)-prodrug were tolerated by the rats. To further define the MTD, overall toxicity was monitored for 14 days. As a sign of toxicity, the body weights of rats were measured. The data are given in FIG. 9. Specifically, FIG. 9 shows the body weight change after treatment with Pt-NP, Pt(IV)-prodrug, cisplatin, and PLGA-PEG-NP.

Figure 10:
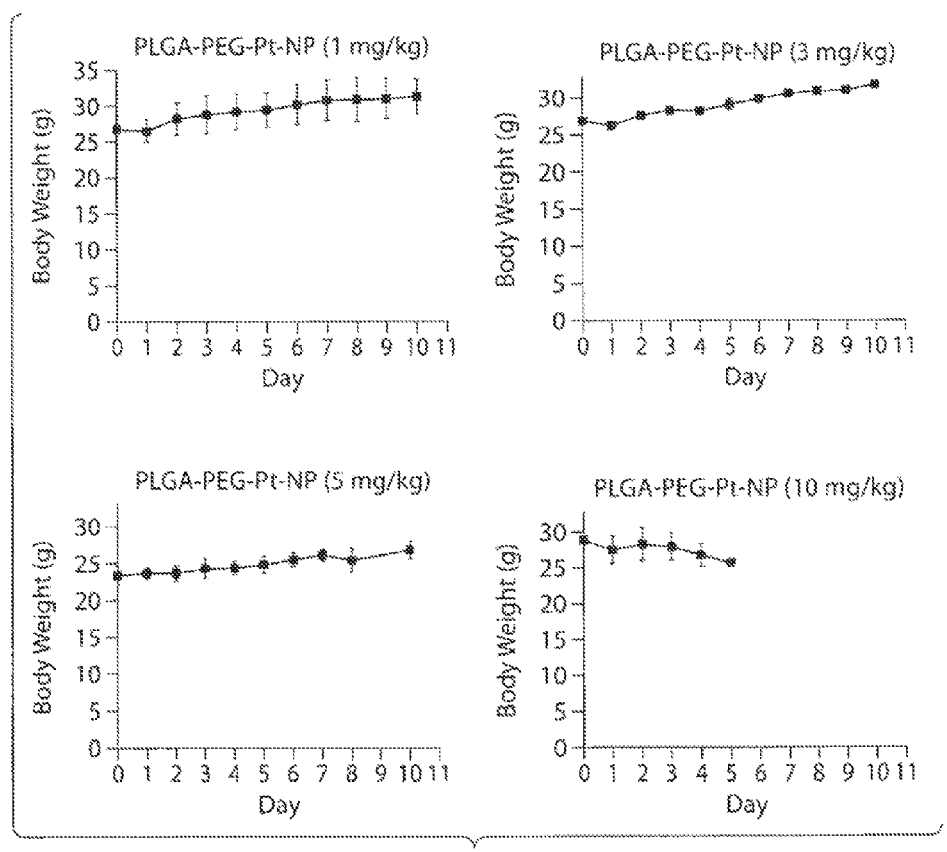
FIG. 10 shows graphs of the maximum therapeutic dose value for Pt-NPs in Swiss Albino mice.

Among the free cisplatin groups, only the rats receiving a dose of 20 mg/kg had significant weight loss, whereas others receiving lower doses did not. Among Pt-NP and PLGA-PEG-NP groups, rats receiving all the different doses show normal weight gain. Among Pt(IV)-prodrug groups, all the rats up to 20 mg/kg did not show any weight loss. Therefore, the MTD for Pt-NP was concluded as 40 mg/kg and that of free cisplatin and Pt(IV)-prodrug as 20 mg/kg. FIG. 10 shows the MTD) value for Pt-NP in Swiss Albino mice was found as 5 mg/kg.

TABLE 2

Maximum Tolerated Dose (MTD) Study in Rats and Mice

| Dose (mg/kg) | No. of Rats | Death |
|---|---|---|
| Pt-NP | | |
| 5 | 3 | 0 |
| 10 | 3 | 0 |
| 20 | 3 | 0 |
| 40 | 3 | 0 |
| 50 | 3 | 2 |
| 60 | 3 | 2 |
| Pt(IV)-prodrug (Compound 1) | | |
| 5 | 3 | 0 |
| 10 | 3 | 0 |
| 20 | 3 | 0 |
| 40 | 3 | 2 |
| Cisplatin | | |
| 5 | 3 | 0 |
| 10 | 3 | 0 |
| 20 | 3 | 0 |
| 40 | 3 | 3 |
| PLGA-PEG-NP | | |
| 5 (100) | 3 | 0 |
| 10 (200) | 3 | 0 |
| 20 (400) | 3 | 0 |
| 40 (800) | 3 | 0 |
| 50 (1000) | 3 | 0 |

EXAMPLE 3

The following example describes non-limiting blood circulation and excretion studies in rats.

Figure 11:
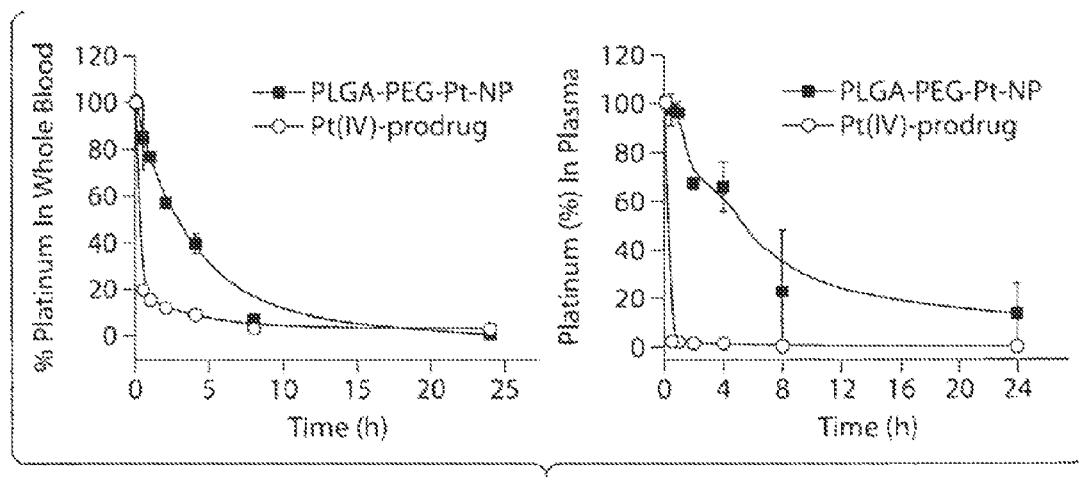
FIG. 11 shows variation of percentage platinum dose in blood with time following the administration of Pt-NPs and Pt(IV)-prodrug intravenously to rat, according to a non-limiting embodiment.

Male Sprague Dawley rats were used in this study. Separate groups of animals received i.v. injections of Pt-NP (2 mg/kg) or Pt(IV)-prodrug (2 mg/kg) and were placed in metabolism cages. Blood was collected at predetermined time points in heparinized tubes. Whole organs or representative tissue samples were removed and weighed where necessary. Urine was collected for 24 h. Plasma was obtained from the blood samples by ultrafugation. Samples were analyzed for their platinum content using a Perkin Elmer Flameless Atomic Absorption Spectrophotometer. The variation of platinum levels in blood with time is shown in FIG. 11. Specifically, FIG. 11 shows variation of percentage platinum dose in blood with time following the administration of Pt-NPs and Pt(IV)-prodrug intravenously to rat.

The entrapment of cisplatin in the form of a prodrug resulted in a significant prolongation of platinum presence in blood. Thus, the platinum dose remaining in the systemic circulation 1 h post administration was 77% in the case of the Pt-NPs, 15.6% in the case of free Pt(IV)-prodrug and literature value for cisplatin is only 1.5%. These non-limiting studies also show that most of the platinum in the blood was plasma bound indicating that the platinum may be available to reach the target tumor sites. The platinum content in the urine samples after 24 h of cumulative accumulation were determined by platinum atomic absorption spectroscopy and found that only 2.9±1.6% of platinum was excreted during this period of time.

EXAMPLE 4

The following example describes non-limiting in vivo anti-tumor activity.

Figure 12A:
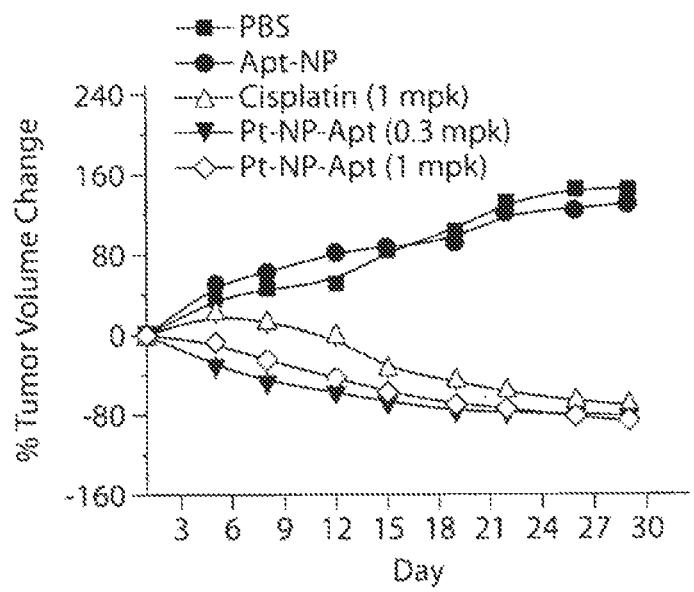
FIG. 12A shows the effect of PBS, cisplatin, NP-Apt, and Pt-NP-Apt on the growth of LNCaP tumor, according to a non-limiting embodiment.
Figure 12B:
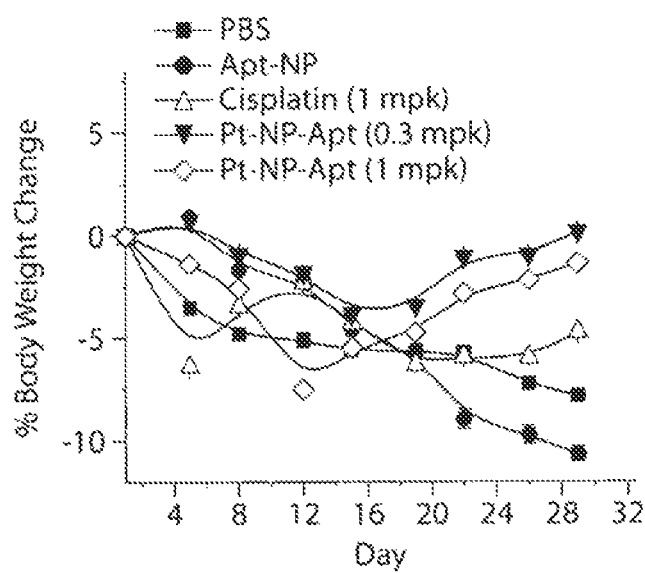
FIG. 12B shows the body weight changed with time of LNCaP-tumor bearing mice treated with PBS, cisplatin, NP-Apt, and Pt-NP-Apt, according to a non-limiting embodiment.

The efficacy of the aptamer-targeted platinum encapsulated nanoparticles (Pt-NP-Apt) was studied using xenograft models of prostate cancer developed by injection of LNCaP cells in the flank of BALB/c nude mice. After tumors had developed to ~100 $mm^3$, comparative efficacy studies were conducted by dividing animals into five groups in a way to minimize weight and tumor size differences among the groups. Using the MTD of 5 mg/kg for i.v. of the construct as a reference point, the following regimens were administered by intravenous injections weekly twice for four weeks: (i) saline; (ii) cisplatin (1 mg/kg), (iii) NP-Apt (20 mg/kg) (nanoparticles without the platinum drug), (iv) Pt-NP-Apt (0.3 mg/kg), and (v) Pt-NP-Apt (1 mg/kg). The tumor size and body weight were then monitored for 30 days. The results showed that administration of Pt-NP-Apt bioconjugate was more efficacious in tumor reduction as compared with NP-Apt cisplatin controls (FIG. 12). Specifically, FIG. 12A shows the effect of PBS, cisplatin, NP-Apt, Pt-NP-Apt on the growth of LNCaP tumor. Each formulation was administered by intravenous injection twice a week for four weeks. FIG. 12B shows the body weight changed with time of LNCaP-tumor bearing mice treated with PBS, cisplatin, NP-Apt, and Pt-NP-Apt. The targeted construct found to be less toxic than cisplatin as demonstrated by the changes in the body weight of the mice.

While several embodiments of the present invention have been described and illustrated herein, those of ordinary skill in the art will readily envision a variety of other means and/or structures for performing the functions and/or obtaining the results and/or one or more of the advantages described herein, and each of such variations and/or modifications is deemed to be within the scope of the present invention. More generally, those skilled in the art will readily appreciate that all parameters, dimensions, materials, and configurations described herein are meant to be exemplary and that the actual parameters, dimensions, materials, and/or configurations will depend upon the specific application or applications for which the teachings of the present invention is/are used. Those skilled in the art will recognize, or be able to ascertain using no more than routine experimentation, many equivalents to the specific embodiments of the invention described herein. It is, therefore, to be understood that the foregoing embodiments are presented by way of example only and that, within the scope of the appended claims and equivalents thereto, the invention may be practiced otherwise than as specifically described and claimed. The present invention is directed to each individual feature, system, article, material, kit, and/or method described herein. In addition, any combination of two or more such features, systems, articles, materials, kits, and/or methods, if such features, systems, articles, materials, kits, and/or methods are not mutually inconsistent, is included within the scope of the present invention.

The indefinite articles "a" and "an," as used herein in the specification and in the claims, unless clearly indicated to the contrary, should be understood to mean "at least one."

The phrase "and/or," as used herein in the specification and in the claims, should be understood to mean "either or both" of the elements so conjoined, i.e., elements that are conjunctively present in some cases and disjunctively present in other cases. Other elements may optionally be present other than the elements specifically identified by the "and/or" clause, whether related or unrelated to those elements specifically identified unless clearly indicated to the contrary. Thus, as a non-limiting example, a reference to "A and/or B," when used in conjunction with open-ended language such as "comprising" can refer, in one embodiment, to A without B (optionally including elements other than B); in another embodiment, to B without A (optionally including elements other than A); in yet another embodiment, to both A and B (optionally including other elements); etc.

As used herein in the specification and in the claims, "or" should be understood to have the same meaning as "and/or" as defined above. For example, when separating items in a list, "or" or "and/or" shall be interpreted as being inclusive, i.e., the inclusion of at least one, but also including more than one, of a number or list of elements, and, optionally, additional unlisted items. Only terms clearly indicated to the contrary, such as "only one of" or "exactly one of," or, when used in the claims, "consisting of," will refer to the inclusion of exactly one element of a number or list of elements. In general, the term "or" as used herein shall only be interpreted as indicating exclusive alternatives (i.e. "one or the other but not both") when preceded by terms of exclusivity, such as "either," "one of," "only one of," or "exactly one of." "Consisting essentially of," when used in the claims, shall have its ordinary meaning as used in the field of patent law.

As used herein in the specification and in the claims, the phrase "at least one," in reference to a list of one or more elements, should be understood to mean at least one element selected from any one or more of the elements in the list of elements, but not necessarily including at least one of each and every element specifically listed within the list of elements and not excluding any combinations of elements in the list of elements. This definition also allows that elements may optionally be present other than the elements specifically identified within the list of elements to which the phrase "at least one" refers, whether related or unrelated to those elements specifically identified. Thus, as a non-limiting example, "at least one of A and B" (or, equivalently, "at least one of A or B," or, equivalently "at least one of A and/or B") can refer, in one embodiment, to at least one, optionally including more than one, A, with no B present (and optionally including elements other than B); in another embodiment, to at least one, optionally including more than one, B, with no A present (and optionally including elements other than A); in yet another embodiment, to at least one, optionally including more than one, A, and at least one, optionally including more than one, B (and optionally including other elements); etc.

In the claims, as well as in the specification above, all transitional phrases such as "comprising," "including," "carrying," "having," "containing," "involving," "holding," and the like are to be understood to be open-ended, i.e., to mean including but not limited to. Only the transitional phrases "consisting of" and "consisting essentially of" shall be closed or semi-closed transitional phrases, respectively, as set forth in the United States Patent Office Manual of Patent Examining Procedures, Section 2111.03.

What is claimed:

1. A method of making a composition for the delivery of a hydrophilic drug comprising:
   providing a hydrophobic drug precursor comprising a substantially hydrophilic small molecule drug bound to a compatibilizing moiety, and
   forming a particle comprising a hydrophobic interior, wherein the hydrophobic drug precursor is encapsulated in the particle in an amount of at least 0.1% by weight based on the weight of the particle.

2. The method of claim 1 further comprising:
   providing a solution comprising the hydrophobic drug precursor and a polymeric base component, and
   contacting the solution with a base component nonsolvent to form the particle.

3. The method of claim 1, wherein the drug comprises a platinum metal compound.

4. The method of claim 3, wherein the drug comprises a platinum (IV) compound or a platinum (II) compound.

5. The method of claim 4, wherein the drug comprises a platinum (IV) compound having the formula

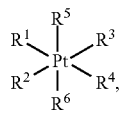

wherein,
$R^1$, $R^2$, $R^3$, and $R^4$ can be the same or different and each is a group comprising at least one of ammonia, an amine, a heterocycle including at least one nitrogen, an aryl group, or a leaving group, any being optionally substituted, or any two or three of $R^1$, $R^2$, $R^3$, and $R^4$ can be joined together to form a bidentate ligang or a tridentate ligand, any being optionally substituted, and $R^5$ and $R^6$ can be the same or different and comprise the formula $-QR^7$, wherein $R^7$ is an alkyl, an alkenyl, an alkynyl, a heteroalkyl, a heteroalkynyl, an aryl, a heteroaryl, or $CO(CH_2)_nCH_3$, wherein n is 0, 1, 2, 3, 4, 5, 6, 7, 8, 9, or 10, and Q is O or N.

6. The method of claim 5, wherein $R^7$ is $CO(CH_2)_nCH_3$, wherein n is an integer from 0 to 10.

7. The method of claim 5, wherein the platinum(IV) compound is

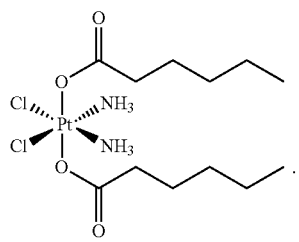

8. The method of claim 5, wherein drug precursor comprises an inorganic metal compound and the compatibilizing moiety is a ligand bound to a metal of the inorganic compound.

9. The method of claim 3, wherein the platinum metal compound is selected from the group consisting of cisplatin, carboplatin, oxaliplatin, [cis-Pt(diaminocyclohexane)Cl$_2$], nedaplatin, stratoplatin, paraplatin, platinol, cycloplatin, dexormaplatin, enloplatin, iproplatin, lobaplatin, ormaplatin, spiroplatin, and zeniplatin.

10. The method of claim 1, wherein the drug is selected from the group consisting of dexamethasone phosphate, nicardipine hydrochloride, methylsalicylic acid, nitroglycerine, hydrophilic serotonin 5-HT3 receptor antagonists, and anthracyclines.

11. The method of claim 1, wherein the drug or drug precursor comprises inorganic or organometallic drugs selected from the group consisting of platinum compounds, ruthenium compounds, cobalt compounds, copper compounds, and iron compounds.

12. The method of claim 1, wherein the compatibilizing moiety comprises at least one of an alkyl, a cycloalkyl, an aryl, or an arylalkyl group.

13. The method of claim 1, further comprising associating the compatibilizing moiety with the drug via a linker prior to forming the particle.

14. The method of claim 13, wherein the linker is selected from the group consisting of CO, SiO, C(O)O, NHC(O)O, and NHCO.

15. The method of claim 2, wherein the polymeric base component is an amphiphilic polymer.

16. The method of claim 2, wherein the polymeric base component comprises a polymer selected from the group consisting of poly(lactic acid), poly(glycolic acid), poly(alkylene glycols), polyhydroxyalkanoates, poly(orthoesters), poly(caprolactones), polylysine, poly(acrylic acid), poly(ethyleneimine), and copolymers thereof.

17. The method of claim 2, wherein the polymeric base component comprises a polymer selected from the group consisting of poly(lactic acid), poly(glycolic acid), poly(lactic-co-glycolic acid), poly(ethylene glycol), and copolymers thereof.

18. The method of claim 2, further comprising associating a targeting moiety with the particle prior to, during, or after formation of the particle.

19. The method of claim 18, wherein the targeting moiety is selected from the group consisting of proteins, peptides, antibodies, and nucleic acids.

20. The method of claim 18, wherein the targeting moiety is prostate specific membrane antigen.

21. The method of claim 1, wherein the particles have an average diameter from about 10 nm to about 200 nm.

22. The method of claim 1, wherein the drug or drug precursor has a molecular weight of not more than about 800 g/mol.

* * * * *